US009279003B2

(12) United States Patent
Park et al.

(10) Patent No.: US 9,279,003 B2
(45) Date of Patent: Mar. 8, 2016

(54) ANALOGS OF SODIUM CHANNEL PEPTIDE TOXIN

(75) Inventors: Jae Hyun Park, Princeton, NJ (US); Donald J. Kyle, Yardley, PA (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

(21) Appl. No.: 13/808,504

(22) PCT Filed: Jul. 7, 2011

(86) PCT No.: PCT/IB2011/001631

§ 371 (c)(1), (2), (4) Date: May 29, 2013

(87) PCT Pub. No.: WO2012/004664

PCT Pub. Date: Jan. 12, 2012

(65) Prior Publication Data

US 2013/0296247 A1 Nov. 7, 2013

Related U.S. Application Data

(60) Provisional application No. 61/362,258, filed on Jul. 7, 2010.

(51) Int. Cl.

| | |
|---|---|
| ***C07K 14/435*** | (2006.01) |
| *A61K 38/00* | (2006.01) |

(52) U.S. Cl.

CPC .......... *C07K 14/43518* (2013.01); *A61K 38/00* (2013.01)

(58) Field of Classification Search

CPC ................................ A61K 38/00; C07K 14/43

See application file for complete search history.

(56) References Cited

U.S. PATENT DOCUMENTS

| | | | |
|---|---|---|---|
| 5,877,026 | A | 3/1999 | Lampe |
| 2015/0191517 | A1 | 7/2015 | Kyle et al. |

OTHER PUBLICATIONS

Clement, et al., "Isolation and characterization of a novel toxin from the venom of the spider Grammostola rosea that blocks sodium channels," *Toxicon 50*(1): 65-74 (Jun. 2007).

Escoubas, et al., "Tarantulas: eight-legged pharmacists and combinatorial chemists," *Toxicon 43* (5): 555-574 (Apr. 2004).

Priest, et al., "ProTx-I and ProTx-II: Gating modifiers of voltage-gated sodium channels," *Toxicon 49* (2): 194-201 (Jan. 2007).

International Search Report and Written Opinion for International Application No. PCT/IB2011/001631, European Patent Office, Netherlands, mailed on Jun. 2, 2012.

International Preliminary Report on Patentability for International Application No. PCT/IB2011/001631, International Bureau of WIPO, Switzerland, mailed on Jan. 8, 2013.

Anger. T., et al., "Medicinal Chemistry of Neuronal Voltage-Gated Sodium Channel Blockers," J. Med. Chem. 44(2):115-137, American Chemical Society, United States (2001).

Baker, M.D. and Wood, J.N., "Involvement of Na+ channels in pain pathways," Trends Pharmacol. Sci. 22(1):27-31, Elsevier Science Ltd., England (2001).

Black, J.A., et al., "Sensory neuron-specific sodium channel SNS is abnormally expressed in the brains of mice with experimental allergic encephalomyelitis and humans with multiple sclerosis," Proc. Natl. Acad. Sci. USA 97(21):11598-11602, National Academy of Sciences, United States (2000).

Brown, C.M., et al., "Neuroprotective properties of lifarizine compared with those of other agents in a mouse model of focal cerebral ischaemia," Br. J. Pharmacol. 115(8):1425-1432, Stockton Press, England (1995).

Cannon, S.C. "Spectrum of Sodium Channel disturbances in the Nondystrophic myotonias and periodic paralyses," Kidney Int. 57(3):772-779, Int. Soc of Neprohlogy, US (2000).

Catterall, W.A., "Common modes of drug action on Na+ channels: local anesthetics, antiarrhythmics and anticonvulsants," Trends Pharmacol. Sci. 8:57-65, Elsevier Science Publishers, B.V., Netherlands (1987).

Chagot, B. et al., Solution structure of Phrixotoxin 1, a specific peptide inhibitor of Kv4 potassium channels from the venom of the theraphosid spider Phrixotrichus, Protein Science 13: 1197-1208 (2004).

Chahine, M., et al., "Voltage-Gated Sodium Channels in Neurological Disorders," CNS Neurol. Disord. Drug Targets 7(2):144-158, Bentham Science Publishers Ltd.,United Arab Emirates (2008).

Clare, J.J., et al., "Voltage-gated sodium channels as therapeutic targets," Drug Discov. Today 5(11):506-520, Elsevier Science Ltd., England (2000).

Donaldson, I., "Tegretol: a double blind trial in tinnitus," J. Laryngol. Otol. 95 (9):947-951, Cambridge University Press, England (1981).

Edgerton, G.B. et al., Evidence for multiple effects of ProTxll on activation gating in NaV1.5, Toxicon 52: 489-500 (2008).

Graham, S.H., et al., "Neuroprotective Effects of a Use-Dependent Blocker of Voltage-Dependent Sodium Channels, BW619C89, in Rat Middle Cerebral Artery Occlusion," J. Pharmacol. Exp. Ther. 269(2):854-859, The American Society for Pharmacology and Experimental Therapeutics, United States (1994).

Hubner, C., et al., "Ion Channel Diseases," Human Molecular Genetics 11:2435-2445, Oxford University Press (2002).

Kyle, D.J., and Ilyin, V.I., "Sodium Channel Blockers," J. Med. Chem. 50(11):2583-2588, American Chemical Society, United States (2007).

(Continued)

*Primary Examiner* — John Ulm

(74) *Attorney, Agent, or Firm* — Purdue Pharma L.P.; Alan L. Koller; Weiying Yang

(57) ABSTRACT

The present invention relates to a peptide and its analogs that selectively inhibit the $Na_v1.7$ sodium channel. The present invention also relates to pharmaceutical compositions useful for treating or preventing a disorder responsive to the blockade of sodium ion channels, especially $Na_v1.7$ sodium ion channels. The present invention further provides methods of treating a disorder responsive to the blockade of sodium channels, and particularly $Na_v1.7$ sodium channels, in a mammal suffering from excess activity of the channels, compositions and methods for providing analgesia by administering a peptide of the invention.

42 Claims, No Drawings

(56) References Cited

OTHER PUBLICATIONS

Lai, J., et al., "The role of voltage-gated sodium channels in neuropathic pain," Curr. Opin. Neurobiol. 13(3):291-297, Elsevier Science Ltd., England (2003).
Lai, J., et al., "Voltage-Gated Sodium Channels and Hyperalgesia," Annu. Rev. Pharmacol. Toxicol. 44:371-397, Annual Reviews, United States (2004).
Laird, J.M.A., et al., "Deficits in Visceral Pain and Referred Hyperalgesia in Nav1.8 (SNS/PN3)-Null Mice," J. Neurosci. 22(19):8352-8356, Society for Neuroscience, United States (2002).
Liu, H., et al., "Mutations in Cardiac Sodium Channels: Clinical Implications," Am. J. Pharmacogenomics 3 (3):173-179, Adis Data Information BV, New Zealand (2003).
Majumdar, B., et al., "An electrocochleographic study of the effects of lignocaine on patients with tinnitus," Clin. Otolaryngol. Allied Sci. 8(3):175-180, Blackwell Scientific Publications, England (1983).
Meisler, M.H. and Kearney, J.A., "Sodium channel mutations in epilepsy and other neurological disorders," J. Clin. Invest. 115(8):2010-2017, American Society for Clinical Investigation, United States (2005).
Middleton, R.E. et al., Biochemistry 41: 14734-14747 (2002).
Moller, A., "Similiarities Between Chronic Pain and Tinnitus," The American Journal of Ontology 18:577-585 (1997).
Nassar, M.A., et al., "Nociceptor-specific gene deletion reveals a major role for Nav1.7 (PN1) in acute and inflammatory pain," Proc. Natl. Acad. Sci. USA 101(34):12706-12711, National Academy of Sciences, United States (2004).
Noble, D., "Unraveling the genetics and mechanisms of cardiac arrhythmia," Proc. Natl. Acad. Sci. USA 99(9):5755-5756, National Academy of Sciences, United States (2002).
Priest, B.T. et al., ProTx-I and ProTx-II: Gating modifiers of voltage-gated sodium channelsToxicon 49: 194-201 (2007).
Schmalhofer, W.A. et al., ProTx-II, a Selective Inhibitor of NaV1.7 Sodium Channels, Blocks Action Potential Propagation in NociceptorsMolecular Pharm. 74: 1476-1481 (2008).
Simpson, J.J. and Davies, W.E., "Recent advances in the pharmacological treatment of tinnitus," Trends Pharmacol. Sci. 20(1):12-18, Elsevier Science, England (1999).
Srivatsa, U., et al., "Mechanisms of Antiarrhythmic Drug Actions and Their Clinical Relevance for Controlling Disorders of Cardiac Rhythm," Curr. Cardiol. Rep. 4(5):401-410, Current Science Inc., United States (2002).
Taylor, C.P. and Meldrum, B.S., "Na+ channels as targets for neuroprotective drugs," Trends Pharmacol. Sci. 16(9):309-316, Elsevier Science Ltd., England (1995).
Toledo-Aral, J.J., et al., "Identification of PN1, a predominant voltage-dependent sodium channel expressed principally in peripheral neurons," Proc. Natl. Acad. Sci. USA 94(4):1527-1532, The National Academy of Sciences, United States (1997).
Wood, J.N., et al., "Voltage-Gated Sodium Channels and Pain Pathways," J. Neurobiol. 61(1):55-71, Wiley Periodicals, Inc., United States (2004).
Yogeeswari, P., et al., "Ion Channels as Important Targets for Antiepileptic Drug Design," Curr. Drug Targets 5 (7):589-602, Bentham Science Publishers Ltd., Netherlands (2004).

SEQUENCE LISTING

```
<160> NUMBER OF SEQ ID NOS: 29

<210> SEQ ID NO 1
<211> LENGTH: 31
<212> TYPE: PRT
<213> ORGANISM: Artificial sequence
<220> FEATURE:
<223> OTHER INFORMATION: Isolated peptide
<220> FEATURE:
<221> NAME/KEY: MISC_FEATURE
<222> LOCATION: (12)..(12)
<223> OTHER INFORMATION: any natural or modified amino acid residue
<220> FEATURE:
<221> NAME/KEY: MISC_FEATURE
<222> LOCATION: (19)..(19)
<223> OTHER INFORMATION: any natural or modified amino acid residue
<220> FEATURE:
<221> NAME/KEY: MISC_FEATURE
<222> LOCATION: (28)..(28)
<223> OTHER INFORMATION: any natural or modified amino acid residue
<220> FEATURE:
<221> NAME/KEY: MISC_FEATURE
<222> LOCATION: (29)..(29)
<223> OTHER INFORMATION: any natural or modified amino acid residue
<220> FEATURE:
<221> NAME/KEY: MISC_FEATURE
<222> LOCATION: (30)..(30)
<223> OTHER INFORMATION: any natural or modified amino acid residue or
      is absent
<220> FEATURE:
<221> NAME/KEY: MISC_FEATURE
<222> LOCATION: (31)..(31)
<223> OTHER INFORMATION: any natural or modified amino acid residue or
      is absent

<400> SEQUENCE: 1

Tyr Cys Gln Lys Trp Met Trp Thr Cys Asp Ser Xaa Arg Lys Cys Cys
1               5                   10                  15

Glu Gly Xaa Val Cys Arg Leu Trp Cys Lys Lys Xaa Xaa Xaa Xaa
            20                  25                  30


<210> SEQ ID NO 2
<211> LENGTH: 30
<212> TYPE: PRT
<213> ORGANISM: Artificial sequence
<220> FEATURE:
<223> OTHER INFORMATION: An embodiment of the present invention
<220> FEATURE:
<221> NAME/KEY: MISC_FEATURE
<222> LOCATION: (30)..(30)
<223> OTHER INFORMATION: tryptophan modified with an amino group

<400> SEQUENCE: 2

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30


<210> SEQ ID NO 3
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 3

Tyr Cys Gln Lys Trp Met Trp Thr Cys Asp Ser Ala Arg Lys Cys Cys
1               5                   10                  15

Glu Gly Met Val Cys Arg Leu Trp Cys Lys Lys Lys Leu Trp
            20                  25                  30
```

<210> SEQ ID NO 4
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 4

```
Tyr Cys Gln Lys Trp Met Trp Thr Cys Asp Ser Glu Arg Lys Cys Cys
1               5                   10                  15

Glu Gly Leu Val Cys Arg Leu Trp Cys Lys Lys Lys Leu Trp
            20                  25                  30
```

<210> SEQ ID NO 5
<211> LENGTH: 29
<212> TYPE: PRT
<213> ORGANISM: Artificial sequence
<220> FEATURE:
<223> OTHER INFORMATION: An embodiment of the present invention

<400> SEQUENCE: 5

```
Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Ile Ile
            20                  25
```

<210> SEQ ID NO 6
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 6

```
Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Leu Trp
            20                  25                  30
```

<210> SEQ ID NO 7
<211> LENGTH: 30
<212> TYPE: PRT
<213> ORGANISM: Artificial sequence
<220> FEATURE:
<223> OTHER INFORMATION: An embodiment of the present invention
<220> FEATURE:
<221> NAME/KEY: MISC_FEATURE
<222> LOCATION: (29)..(29)
<223> OTHER INFORMATION: alpha-methylated leucine residue

<400> SEQUENCE: 7

```
Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Leu Trp
            20                  25                  30
```

<210> SEQ ID NO 8
<211> LENGTH: 30
<212> TYPE: PRT
<213> ORGANISM: Artificial sequence
<220> FEATURE:
<223> OTHER INFORMATION: An embodiment of the present invention
<220> FEATURE:
<221> NAME/KEY: MISC_FEATURE
<222> LOCATION: (29)..(29)

<223> OTHER INFORMATION: N-methylated leucine residue

<400> SEQUENCE: 8

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Leu Trp
            20                  25                  30

<210> SEQ ID NO 9
<211> LENGTH: 31
<212> TYPE: PRT
<213> ORGANISM: Artificial sequence
<220> FEATURE:
<223> OTHER INFORMATION: An embodiment of the present invention

<400> SEQUENCE: 9

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Ile Leu Trp
            20                  25                  30

<210> SEQ ID NO 10
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 10

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Leu Ile
            20                  25                  30

<210> SEQ ID NO 11
<211> LENGTH: 30
<212> TYPE: PRT
<213> ORGANISM: Artificial sequence
<220> FEATURE:
<223> OTHER INFORMATION: An embodiment of the present invention
<220> FEATURE:
<221> NAME/KEY: MISC_FEATURE
<222> LOCATION: (29)..(29)
<223> OTHER INFORMATION: alpha-methylated leucine residue

<400> SEQUENCE: 11

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Lys Leu Ile
            20                  25                  30

<210> SEQ ID NO 12
<211> LENGTH: 30
<212> TYPE: PRT
<213> ORGANISM: Artificial sequence
<220> FEATURE:
<223> OTHER INFORMATION: An embodiment of the present invention
<220> FEATURE:
<221> NAME/KEY: MISC_FEATURE
<222> LOCATION: (29)..(29)
<223> OTHER INFORMATION: N-methylated leucine residue

<400> SEQUENCE: 12

Tyr Cys Gln Lys Trp Met Trp Thr Cys Asp Ser Ala Arg Lys Cys Cys
1               5                   10                  15

-continued

```
Glu Gly Leu Val Cys Arg Leu Trp Cys Lys Lys Lys Leu Ile
            20                  25                  30


<210> SEQ ID NO 13
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 13

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile Leu Trp
            20                  25                  30


<210> SEQ ID NO 14
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 14

Tyr Cys Gln Lys Trp Met Trp Thr Cys Asp Ser Ala Arg Lys Cys Cys
1               5                   10                  15

Glu Gly Leu Val Cys Arg Leu Trp Cys Lys Lys Ile Ile Trp
            20                  25                  30


<210> SEQ ID NO 15
<211> LENGTH: 29
<212> TYPE: PRT
<213> ORGANISM: Artificial sequence
<220> FEATURE:
<223> OTHER INFORMATION: An embodiment of the present invention

<400> SEQUENCE: 15

Thr Cys Gln Lys Trp Met Trp Thr Cys Asp Ser Ala Arg Lys Cys Cys
1               5                   10                  15

Glu Gly Leu Val Cys Arg Leu Trp Cys Lys Lys Leu Trp
            20                  25


<210> SEQ ID NO 16
<211> LENGTH: 30
<212> TYPE: PRT
<213> ORGANISM: Artificial sequence
<220> FEATURE:
<223> OTHER INFORMATION: Protoxin II

<400> SEQUENCE: 16

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Trp
            20                  25                  30


<210> SEQ ID NO 17
<211> LENGTH: 29
<212> TYPE: PRT
<213> ORGANISM: Grammostola spatulata
<220> FEATURE:
<223> OTHER INFORMATION: Phrixotoxin I

<400> SEQUENCE: 17

Tyr Cys Gln Lys Trp Met Trp Thr Cys Asp Ser Ala Arg Lys Cys Cys
1               5                   10                  15
```

Glu Gly Leu Val Cys Arg Leu Trp Cys Lys Lys Ile Ile
20 25

<210> SEQ ID NO 18
<211> LENGTH: 29
<212> TYPE: PRT
<213> ORGANISM: Chilobrachys jingzhao
<220> FEATURE:
<223> OTHER INFORMATION: JzTx XII

<400> SEQUENCE: 18

Tyr Cys Gln Lys Trp Met Trp Thr Cys Asp Ser Glu Arg Leu Cys Cys
1 5 10 15

Glu Gly Tyr Val Cys Glu Leu Trp Cys Lys Tyr Asn Leu
20 25

<210> SEQ ID NO 19
<211> LENGTH: 29
<212> TYPE: PRT
<213> ORGANISM: Grammostola spatulata
<220> FEATURE:
<223> OTHER INFORMATION: GsAF I

<400> SEQUENCE: 19

Tyr Cys Gln Lys Trp Leu Trp Thr Cys Asp Ser Glu Arg Lys Cys Cys
1 5 10 15

Glu Asp Met Val Cys Arg Leu Trp Cys Lys Lys Arg Leu
20 25

<210> SEQ ID NO 20
<211> LENGTH: 29
<212> TYPE: PRT
<213> ORGANISM: Chilobrachys jingzhao
<220> FEATURE:
<223> OTHER INFORMATION: JzTx V

<400> SEQUENCE: 20

Tyr Cys Gln Lys Trp Met Trp Thr Cys Asp Ser Lys Arg Ala Cys Cys
1 5 10 15

Glu Gly Leu Arg Cys Lys Leu Trp Cys Arg Lys Ile Ile
20 25

<210> SEQ ID NO 21
<211> LENGTH: 32
<212> TYPE: PRT
<213> ORGANISM: Grammostola rosea
<220> FEATURE:
<223> OTHER INFORMATION: VsTx II

<400> SEQUENCE: 21

Tyr Cys Gln Lys Trp Met Trp Thr Cys Asp Glu Glu Arg Lys Cys Cys
1 5 10 15

Glu Gly Leu Val Cys Arg Leu Trp Cys Lys Lys Lys Ile Glu Glu Gly
20 25 30

<210> SEQ ID NO 22
<211> LENGTH: 31
<212> TYPE: PRT
<213> ORGANISM: Grammostola spatulata
<220> FEATURE:
<223> OTHER INFORMATION: GsAF II

<400> SEQUENCE: 22

Tyr Cys Gln Lys Trp Met Trp Thr Cys Asp Glu Glu Arg Lys Cys Cys

```
1               5                   10                  15

Glu Gly Leu Val Cys Arg Leu Trp Cys Lys Lys Lys Ile Glu Trp
            20                  25                  30


<210> SEQ ID NO 23
<211> LENGTH: 29
<212> TYPE: PRT
<213> ORGANISM: Grammostola spatulata
<220> FEATURE:
<223> OTHER INFORMATION: GrTx I

<400> SEQUENCE: 23

Tyr Cys Gln Lys Trp Met Trp Thr Cys Asp Ser Lys Arg Lys Cys Cys
1               5                   10                  15

Glu Asp Met Val Cys Gln Leu Trp Cys Lys Lys Arg Leu
            20                  25


<210> SEQ ID NO 24
<211> LENGTH: 31
<212> TYPE: PRT
<213> ORGANISM: Grammostola spatulata
<220> FEATURE:
<223> OTHER INFORMATION: GsMtx II / PaTx II

<400> SEQUENCE: 24

Tyr Cys Gln Lys Trp Met Trp Thr Cys Asp Glu Glu Arg Lys Cys Cys
1               5                   10                  15

Glu Gly Leu Val Cys Arg Leu Trp Cys Lys Arg Ile Ile Asn Met
            20                  25                  30


<210> SEQ ID NO 25
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 25

Tyr Cys Gln Lys Trp Met Trp Thr Cys Asp Ser Ala Arg Lys Cys Cys
1               5                   10                  15

Glu Gly Met Val Cys Arg Leu Trp Cys Lys Lys Lys Leu Trp
            20                  25                  30


<210> SEQ ID NO 26
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 26

Tyr Cys Gln Lys Trp Met Trp Thr Cys Asp Ser Glu Arg Lys Cys Cys
1               5                   10                  15

Glu Gly Ala Val Cys Arg Leu Trp Cys Lys Lys Lys Leu Trp
            20                  25                  30


<210> SEQ ID NO 27
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 27
```

-continued

```
Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Ala Leu Trp
            20                  25                  30


<210> SEQ ID NO 28
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 28

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Ala Trp
            20                  25                  30


<210> SEQ ID NO 29
<211> LENGTH: 30
<212> TYPE: PRT
<213> ORGANISM: Artificial sequence
<220> FEATURE:
<223> OTHER INFORMATION: An embodiment of the present invention

<400> SEQUENCE: 29

Tyr Cys Gln Lys Trp Met Trp Thr Cys Asp Ser Glu Arg Lys Cys Cys
1               5                   10                  15

Glu Gly Met Val Cys Arg Leu Trp Cys Lys Lys Lys Leu Ala
            20                  25                  30
```

ANALOGS OF SODIUM CHANNEL PEPTIDE TOXIN

REFERENCE TO SEQUENCE LISTING SUBMITTED ELECTRONICALLY VIA EFS-WEB

This application includes a "Sequence Listing_ascii.txt," 12,433 bytes, created on Jul. 22, 2013, and submitted electronically via EFS-Web, which is hereby incorporated by reference in its entirety.

BACKGROUND OF THE INVENTION

1. Field of the Invention

This invention is in the field of peptide chemistry. The invention relates to novel peptides and the use of these peptides as blockers of sodium ($Na^+$) channels.

2. Background Art

Voltage-gated sodium channels (VGSCs) are found in all excitable cells. In neuronal cells of the central nervous system (CNS) and peripheral nervous system (PNS), sodium channels are primarily responsible for generating the rapid upstroke of the action potential. In this manner, sodium channels are essential to the initiation and propagation of electrical signals in the nervous system. Proper function of sodium channels is therefore necessary for normal function of the neuron. Consequently, aberrant sodium channel function is thought to underlie a variety of medical disorders (See Hubner et al., *Hum. Mol. Genet.* 11:2435-2445 (2002) for a general review of inherited ion channel disorders) including epilepsy (Yogeeswari et al, *Curr. Drug Target* 5:589-602 (2004)), arrhythmia (Noble, Proc. *Natl. Acad. Sci. USA* 99:5755-5756 (2002)), myotonia (Cannon, *Kidney Int.* 57:772-779 (2000)), and pain (Wood et al., *J. Neurobiol.,* 61:55-71 (2004)).

VGSCs are composed of one α-subunit, which forms the core of the channel and is responsible for voltage-dependent gating and ion permeation, and several auxiliary β-subunits (see, e.g., Chahine et al., *CNS & Neurological Disorders-Drug Targets* 7:144-158 (2008) and Kyle and Ilyin., *J. Med. Chem.* 50:2583-2588 (2007)). α-Subunits are large proteins composed of four homologous domains. Each domain contains six α-helical transmembrane spanning segments. There are currently 9 known members of the family of voltage-gated sodium channel α-subunits. Names for this family include SCNx, SCNAx, and $Na_v$x.x (see Table 1, below). The VGSC family has been phylogenetically divided into two subfamilies $Na_v$1.x (all but SCN6A) and $Na_v$2.x (SCN6A). The $Na_v$1.x subfamily can be functionally subdivided into two groups, those which are sensitive to blocking by tetrodotoxin (TTX-sensitive or TTX-s) and those which are resistant to blocking by tetrodotoxin (TTX-resistant or TTX-r).

There are three members of the subgroup of TTX-resistant sodium channels. The SCN5A gene product ($Na_v$1.5, H1) is almost exclusively expressed in cardiac tissue and has been shown to underlie a variety of cardiac arrhythmias and other conduction disorders (Liu et al., *Am. J. Pharmacogenomics* 3:173-179 (2003)). Consequently, blockers of $Na_v$1.5 have found clinical utility in treatment of such disorders (Srivatsa et al., *Curr. Cardiol. Rep.* 4:401-410 (2002)). The remaining TTX-resistant sodium channels, $Na_v$1.8 (SCN10A, PN3, SNS) and $Na_v$1.9 (SCN11A, NaN, SNS2) are expressed in the peripheral nervous system and show preferential expression in primary nociceptive neurons. Human genetic variants of these channels have not been associated with any inherited clinical disorder. However, aberrant expression of $Na_v$1.8 has been found in the CNS of human multiple sclerosis (MS) patients and also in a rodent model of MS (Black et al., *Proc. Natl. Acad. Sci. USA* 97:11598-115602 (2000)). Evidence for involvement in nociception is both associative (preferential expression in nociceptive neurons) and direct (genetic knockout). $Na_v$1.8-null mice exhibited typical nociceptive behavior in response to acute noxious stimulation but had significant deficits in referred pain and hyperalgesia (Laird et al., *J. Neurosci.* 22:8352-8356 (2002)).

TABLE 1

Voltage-gated sodium channel gene family

| Type | Gene Symbol | Tissue Distribution | TTX $IC_{50}$ (nM) | Disease Association | Indications |
|---|---|---|---|---|---|
| $Na_v$1.1 | SCN1A | CNS/PNS | 10 | Epilepsy | Pain, seizures, neurodegeneration |
| $Na_v$1.2 | SCN2A | CNS | 10 | Epilepsy | Epilepsy, neurodegeneration |
| $Na_v$1.3 | SCN3A | CNS | 15 | — | Pain |
| $Na_v$1.4 | SCN4A | Skeletal muscle | 25 | Myotonia | Myotonia |
| $Na_v$1.5 | SCN5A | Heart muscle | 2,000 | Arrhythmia | Arrhythmia |
| $Na_v$1.6 | SCN8A | CNS/PNS | 6 | — | Pain, movement disorders |
| $Na_v$1.7 | SCN9A | PNS | 25 | Erythermalgia | Pain |
| $Na_v$1.8 | SCN10A | PNS | 50,000 | — | Pain |
| $Na_v$1.9 | SCN11A | PNS | 1,000 | — | Pain |

The $Na_v$1.7 (PN1, SCN9A) VGSC is sensitive to blocking by tetrodotoxin and is preferentially expressed in peripheral sympathetic and sensory neurons. The SCN9A gene has been cloned from a number of species, including human, rat, and rabbit and shows ~90% amino acid identity between the human and rat genes (Toledo-Aral et al., *Proc. Natl. Acad. Sci. USA* 94:1527-1532 (1997)).

An increasing body of evidence suggests that $Na_v$1.7 may play a key role in various pain states, including acute, inflammatory and/or neuropathic pain. Deletion of the SCN9A gene in nociceptive neurons of mice led to an increase in mechanical and thermal pain thresholds and reduction or abolition of inflammatory pain responses (Nassar et al., *Proc. Natl. Acad. Sci. USA* 101:12706-12711 (2004)).

Sodium channel-blocking agents have been reported to be effective in the treatment of various disease states, and have found particular use as local anesthetics, e.g., lidocaine and bupivacaine, and in the treatment of cardiac arrhythmias, e.g., propafenone and amiodarone, and epilepsy, e.g., lamotrigine, phenyloin and carbamazepine (see Clare et al., *Drug Discovery Today* 5:506-510 (2000); Lai et al., *Annu. Rev. Pharmacol. Toxicol.* 44:371-397 (2004); Anger et al., *J. Med. Chem.* 44:115-137 (2001), and Catterall, *Trends Pharmacol. Sci.* 8:57-65 (1987)). Each of these agents is believed to act by interfering with the rapid influx of sodium ions.

Other sodium channel blockers such as BW619C89 and lifarizine have been shown to be neuroprotective in animal models of global and focal ischemia (Graham et al., *J. Pharmacol. Exp. Ther.* 269:854-859 (1994); Brown et al., British *J. Pharmacol.* 115:1425-1432 (1995)).

It has also been reported that sodium channel-blocking agents may be useful in the treatment of pain, including acute, chronic, inflammatory, neuropathic, and other types of pain such as rectal, ocular, and submandibular pain typically associated with paroxysmal extreme pain disorder; see, for example, Kyle and Ilyin, *J. Med. Chem.* 50:2583-2588 (2007); Wood et al., *J. Neurobiol.* 61:55-71 (2004); Baker et al., *TRENDS in Pharmacological Sciences* 22:27-31 (2001); and Lai et al., *Current Opinion in Neurobiology* 13:291-297 (2003); the treatment of neurological disorders such as epilepsy, seizures, epilepsy with febrile seizures, epilepsy with benign familial neonatal infantile seizures, inherited pain disorders, e.g., primary erythermalgia and paroxysmal extreme pain disorder, familial hemiplegic migraine, and movement disorder; and the treatment of other psychiatric disorders such as autism, cerebeller atrophy, ataxia, and mental retardation; see, for example, Chahine et al., *CNS & Neurological Disorders-Drug Targets* 7:144-158 (2008) and Meisler and Kearney, *J. Clin. Invest.* 115:2010-2017 (2005). In addition to the above-mentioned clinical uses, carbamazepine, lidocaine and phenyloin are occasionally used to treat neuropathic pain, such as from trigeminal neuralgia, diabetic neuropathy and other forms of nerve damage (Taylor and Meldrum, *Trends Pharmacol. Sci.* 16:309-316 (1995)). Furthermore, based on a number of similarities between chronic pain and tinnitus (Moller, *Am. J. Otol.* 18:577-585 (1997); Tonndorf, *Hear. Res.* 28:271-275 (1987)), it has been proposed that tinnitus may be viewed as a form of chronic pain sensation (Simpson, et al., *Tip.* 20:12-18 (1999)). Indeed, lidocaine and carbamazepine have been shown to be efficacious in treating tinnitus (Majumdar, B. et al., *Clin. Otolaryngol.* 8:175-180 (1983); Donaldson, *Laryngol. Otol.* 95:947-951 (1981)).

The polypeptide toxins from the tarantula *Thrixopelma pruriens* (protoxins) are members of the inhibitory cysteine-knot family of protein toxins, which contain 30 to 35 amino acid residues and three disulfide bridges. Protoxin I (ProTx I) and Protoxin II (ProTx II) are *T. pruriens* peptide toxins that have three cystine bridges in the connectivity pattern $C_2$ to $C_{16}$, $C_9$ to $C_{21}$, and $C_{15}$ to $C_{25}$. For example, Protoxin II (SEQ ID NO: 16) has cystine bridges as follows:

YCQKWMWTCDSERKCCEGMVCRLWCKKKLW

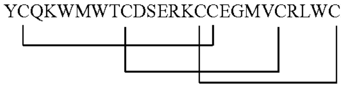

ProTx I and ProTx II inhibit activation of sodium channels (Middleton, R. E. et al., *Biochemistry* 41: 14734-14747 (2002)). ProTx I and ProTx II act as gating modifiers that prevent channel activation via a voltage sensor-trapping mechanism (Edgerton, G. B. et al., *Toxicon* 52: 489-500 (2008); Priest, B. T. et al., *Toxicon* 49: 194-201 (2007)). ProTx II inhibits $Na_v1.7$ sodium channels (Schmalhofer, W. A. et al., *Molecular Pharm.* 74: 1476-1481 (2008)).

Phrixotoxin I (PaTx I) is a *Grammostola spatulata* spider toxin that acts as a gating modifier of Kv4 potassium channels (Chagot, B. et al., *Protein Science* 13: 1197-1208 (2004)). GrTx1 is a toxin isolated from *Grammostola spatulata* that blocks sodium channels (Clement, H. et al., *Toxicon* 50: 65-74 (2007)).

Many patients with either acute or chronic pain disorders respond poorly to current pain therapies, and developing resistance or insensitivity to opiates is common. In addition, many of the currently available treatments have undesirable side effects. Thus, there remains a need for more effective and safer analgesics that work by blocking sodium channels.

BRIEF SUMMARY OF THE INVENTION

The present invention provides the peptides disclosed herein, and the pharmaceutically acceptable salts, prodrugs and solvates thereof, which are useful as blockers of sodium ($Na^+$) channels, and particularly $Na_v1.7$ channels. These peptides, which comprise the amino acid sequence of SEQ ID NO: 1, show selectivity as $Na_v1.7$ channel blockers relative to $Na_v1.2$.

The present invention further provides pharmaceutical compositions comprising an effective amount of a peptide comprising an amino acid sequence of SEQ ID NO: 1, or a pharmaceutically acceptable salt, prodrug or solvate thereof, in a mixture with one or more pharmaceutically acceptable carriers. Pharmaceutical compositions of the present invention are useful for treating or preventing a disorder responsive to the blockade of sodium ion channels, especially $Na_v1.7$ sodium ion channels.

The present invention further provides methods of treating a disorder responsive to the blockade of sodium channels, and particularly $Na_v1.7$ sodium channels, in a mammal suffering from excess activity of said channels, said methods comprising administering to said mammal an effective amount of a peptide comprising the amino acid sequence of SEQ ID NO: 1, or a pharmaceutically acceptable salt, prodrug or solvate thereof, as described herein. In a preferred embodiment, the disorder being treated is pain (e.g., acute pain, chronic pain, or inflammatory pain, which includes but is not limited to, neuropathic pain and surgical pain).

The present invention further provides a method of preventing a disorder responsive to the blockade of sodium channels, and particularly $Na_v1.7$ sodium channels, in a mammal at risk of suffering from excess activity of said channels, said method comprising administering to said mammal an effective amount of a peptide comprising the amino acid sequence of SEQ ID NO: 1, or a pharmaceutically acceptable salt, prodrug or solvate thereof, as described herein. In a preferred embodiment, the disorder being prevented is pain (e.g., acute pain, chronic pain, or inflammatory pain, which includes but is not limited to, neuropathic pain and surgical pain).

The present invention further provides the use of a peptide comprising the amino acid sequence of SEQ ID NO: 1, or a pharmaceutically acceptable salt, prodrug or solvate thereof, in the manufacture of a medicament useful to treat or prevent a disorder responsive to the blockade of sodium channels, and particularly $Na_v1.7$ sodium channels. In a preferred embodiment, the disorder being treated or prevented is pain (e.g., acute pain, chronic pain, or inflammatory pain, which includes but is not limited to, neuropathic pain and surgical pain).

The present invention further provides a method of modulating the activity of sodium ion channels, especially $Na_v1.7$ sodium ion channels, in a cell, or in a membrane preparation, which method comprises administering to the cell or membrane preparation an effective amount of a peptide comprising the amino acid sequence of SEQ ID NO: 1, or a pharmaceutically acceptable salt, prodrug or solvate thereof. In certain embodiments, the method is carried out in an in vitro cellular or membrane assay system. In other embodiments, the method is carried out in an in vivo system, e.g., in a mammal such as a human.

The present invention further provides radiolabeled peptides comprising the amino acid sequence of SEQ ID NO: 1, and the use of such radiolabeled peptides as radioligands for use in any appropriately selected competitive binding assays and screening methodologies Thus, the present invention further provides a method for screening a candidate peptide for its ability to bind to a sodium channel or sodium channel subunit using a radiolabeled peptide of the present invention. In certain embodiments, the peptide is radiolabeled with $^3H$, $^{11}C$ or $^{14}C$. This competitive binding assay can be conducted using any appropriately selected screening methodology. In one embodiment, the screening methodology comprises: i) introducing a fixed concentration of the radiolabeled peptide to an in vitro preparation comprising a soluble or membrane-associated sodium channel, subunit or fragment thereof under conditions that permit the radiolabeled peptide to bind to the channel, subunit or fragment, respectively, to form a conjugate; ii) titrating the mixture with a candidate peptide; and iii) determining the ability of the candidate peptide to displace the radiolabeled peptide from said channel, subunit or fragment.

It is to be understood that both the foregoing summary and the following detailed description are exemplary and explanatory only and are not necessarily restrictive of the invention as claimed.

DETAILED DESCRIPTION OF THE INVENTION

As used herein, the term "amino acid residue" refers to a specific amino acid, usually dehydrated as a result of its involvement in two peptide bonds or in a polypeptide backbone, but also when the amino acid is involved in one peptide bond, as occurs at each end of a linear polypeptide chain. The amino acid residues may be referred to by the commonly accepted three-letter codes or single-letter codes as known in the art. The amino acid residues and amino acids as described herein may be in their D- or L-form, and in one embodiment are in their L-form.

As used herein, a "prodrug" of a peptide of the present invention is converted to the peptide of the present invention via an enzymatic reaction, typically under physiological conditions in the living body, that is, conversion from the prodrug to the peptide occurs by enzymatically catalyzed oxidation, reduction, or hydrolysis, etc. Methods for making peptide prodrugs are known in the art. For example, see Oliyai, R., *Advanced Drug Delivery Reviews* 19: 275-286 (1996); Oliyai, R. et al., *Ann. Rev. Pharmcol. Toxicol.* 32: 521-44 (1993); Paulette, G. M. et al., *Advanced Drug Delivery Reviews* 27: 235-256 (1997); Han, H.-K., *AAPS Pharmsci* 2: 1-11 (2000); Prokai, L. *Expert Opinion On Therapeutic Patents* 7: 233-245 (1997).

As used herein, the term "an isolated peptide comprising" encompasses peptides containing the indicated amino acid sequence (e.g. SEQ ID NO: 1) plus additional amino acids at the C-terminus and/or N-terminus of said amino acid sequence, as well as peptides consisting of the indicated amino acid sequence. In a specific aspect, the peptide of present invention contains, for example, 10, 9, 8, 7, 6, 5, 4, 3, 2, or 1 amino acids in addition to the indicated amino acid sequence. In a further specific aspect, the peptide of present invention contains not more than 10, 9, 8, 7, 6, 5, 4, 3, 2, or 1 amino acids in addition to the indicated amino acid sequence. In a further specific aspect, the peptide of present invention consists of the indicated amino acid sequence, i.e. it does not contain any additional amino acids.

As used in the context of present invention, the singular forms of "a" and "an" also include the respective plurals unless the context clearly dictates otherwise.

The term "about" in context with a numerical value or parameter range denotes an interval of accuracy that the person skilled in the art will understand to still ensure the technical effect of the feature in question. The term typically indicates deviation from the indicated numerical value of +/−10%, preferably +/−5%.

The present invention is based on the use of peptides comprising the amino acid sequence of SEQ ID NO: 1 and the pharmaceutically acceptable salts, prodrugs and solvates thereof (collectively referred to hereinafter as "peptides of the invention"), as blockers of $Na^+$ channels. In view of this property, peptides of the invention are useful for treating or preventing disorders that can be treated or prevented by the blockade of sodium ion channels. In one aspect, peptides of the invention selectively block $Na_v1.7$ sodium ion channels compared to other sodium channels, and are therefore useful for treating or preventing disorders responsive to the selective blockade of $Na_v1.7$ sodium ion channels.

In a specific aspect, a peptide of the present invention selectively blocks a $Na_v1.7$ sodium ion channel, compared to a $Na_v1.2$ sodium channel. Selectivity of a peptide for a $Na_v1.7$ channel, compared to a $Na_v1.2$ channel, means that the peptide shows selectivity in one of the assays described herein, e.g. a lower $IC_{50}$ value. Thus, the ratio of binding to $Na_v1.7$ versus binding to $Na_v1.2$ is greater than 1, typically greater than about 2 and can reach values of about 40 and more. In particular, the ratio may range from about 2 to about 500, from about 2 to about 100, from about 3 to about 50, from about 8 to about 40, or have any numerical value within these ranges. For example, the $IC_{50}$ for $Na_v1.2$ in comparison to the $IC_{50}$ for $Na_v1.7$ may have these ratio ranges, as exemplified in the Examples.

Likewise, when comparing the $IC_{50}$, the phrase "selectivity for a $Na_v1.7$ sodium channel over a $Na_v1.2$ sodium channel" is used herein to mean that the ratio of an $IC_{50}$ for $Na_v1.7$ sodium channel blocking activity for a peptide of the invention over an $IC_{50}$ for $Na_v1.2$ sodium channel blocking activity for the same peptide is less than 1, i.e., $Na_v1.7\ IC_{50}/Na_v1.2\ IC_{50}<1$. Preferably, a peptide of the invention exhibits an $Na_v1.7\ IC_{50}/Na_v1.2\ IC_{50}$ ratio of about 1/2, 1/3, 1/4, 1/5, 1/6, 1/7, 1/8, 1/9, 1/10, 1/15, 1/20, 1/25, 1/30, 1/35, 1/40, 1/45, 1/50, 1/55, 1/60, 1/65, 1/70, 1/75, 1/80, 1/85, 1/90, 1/95, 1/100, 1/125, 1/150, 1/175, 1/200, 1/225, 1/250, 1/275, 1/300, 1/325, 1/350, 1/375, 1/400, 1/425, 1/450, 1/475 or 1/500 or less.

The peptides of the invention may be in their linear form or they may contain one, two or three cystine bridges (disulfide bridges). The connectivity of these one, two or three cystine bridges is preferably selected from the group consisting of $C_2$ to $C_{16}$, $C_9$ to $C_{21}$ and $C_{15}$ to $C_{25}$ (i.e. the Cys at position 2 is connected to the Cys at position 16 etc.). In one embodiment, the peptides of the invention contain three cystine bridges with the connectivity $C_2$ to $C_{16}$, $C_9$ to $C_{21}$ and $C_{15}$ to $C_{25}$.

The present invention provides an isolated peptide comprising the following amino acid sequence:

(SEQ ID NO: 1)

$Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Xaa_{12}$-$Arg_{13}$-$Lys_{14}$-

$Cys_{15}$-$Cys_{16}$-$Glu_{17}$-$Gly_{18}$-$Xaa_{19}$-$Val_{20}$-$Cys_{21}$-$Arg_{22}$-$Leu_{23}$-$Trp_{24}$-$Cys_{25}$-$Lys_{26}$-

$Lys_{27}$-$Xaa_{28}$-

$Xaa_{29}$-$Xaa_{30}$-$Xaa_{31}$, and the pharmaceutically acceptable salts, prodrugs and solvates thereof, wherein each of $Xaa_{12}$, $Xaa_{19}$, $Xaa_{28}$ and $Xaa_{29}$ is any natural or modified amino acid residue;

$Xaa_{30}$ is any natural or modified amino acid residue or is absent; and $Xaa_{31}$ is any natural or modified amino acid residue or is absent;

wherein the isolated peptide does not comprise the amino acid sequence of SEQ ID NO: 25, SEQ ID NO: 26, SEQ ID NO: 27, SEQ ID NO: 28, or SEQ ID NO: 29, and wherein the isolated peptide does not comprise the amino acid sequence of ProTx II (SEQ ID NO: 16) or PaTx I (SEQ ID NO: 17).

In one embodiment, the present invention provides an isolated peptide comprising the amino acid sequence of SEQ ID NO: 2, 4, 5, 6, 7, 8, 9, 10, 11, 12, 13, 14 or 15.

In another embodiment, the present invention provides an isolated peptide comprising the amino acid sequence of SEQ ID NO: 1, wherein $Xaa_{12}$ is an alanine residue; each of $Xaa_{19}$, $Xaa_{28}$ and $Xaa_{29}$ is any natural or modified amino acid residue; $Xaa_{30}$ is any natural or modified amino acid residue or is absent; and $Xaa_{31}$ is absent.

In another embodiment, the present invention provides an isolated peptide comprising the amino acid sequence of SEQ ID NO: 1, wherein $Xaa_{19}$ is a leucine residue; each of $Xaa_{12}$, $Xaa_{28}$ and $Xaa_{29}$ is any natural or modified amino acid residue; $Xaa_{30}$ is any natural or modified amino acid residue or is absent; and $Xaa_{31}$ is absent.

In another embodiment, the present invention provides an isolated peptide comprising the amino acid sequence of SEQ ID NO: 1, wherein $Xaa_{12}$ is an alanine residue; $Xaa_{19}$ is a leucine residue; each of $Xaa_{28}$ and $Xaa_{29}$ is any natural or modified amino acid residue; $Xaa_{30}$ is any natural or modified amino acid residue or is absent; and $Xaa_{31}$ is absent.

In another embodiment, the present invention provides an isolated peptide comprising the amino acid sequence of SEQ ID NO: 1, wherein $Xaa_{12}$ is a glutamate residue, $Xaa_{19}$ is a methionine residue, $Xaa_{28}$ is a lysine residue, $Xaa_{29}$ is a leucine residue, $Xaa_{30}$ is tryptophan modified with an amino group, and $Xaa_{31}$ is absent (SEQ ID NO: 2).

In another embodiment, the present invention provides an isolated peptide comprising the amino acid sequence of SEQ ID NO: 1, wherein $Xaa_{12}$ is a glutamate residue, $Xaa_{19}$ is a leucine residue, $Xaa_{28}$ is a lysine residue, $Xaa_{29}$ is a leucine residue, $Xaa_{30}$ is a tryptophan residue, and $Xaa_{31}$ is absent (SEQ ID NO: 4).

In another embodiment, the present invention provides an isolated peptide comprising the amino acid sequence of SEQ ID NO: 1, wherein $Xaa_{12}$ is a glutamate residue, $Xaa_{19}$ is a methionine residue, $Xaa_{28}$ is an isoleucine residue, $Xaa_{29}$ is an isoleucine residue, $Xaa_{30}$ is absent, and $Xaa_{31}$ is absent (SEQ ID NO: 5).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is a leucine residue, $Xaa_{30}$ is a tryptophan residue, and $Xaa_{31}$ is absent (SEQ ID NO: 6).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is a tryptophan residue, and $Xaa_{31}$ is absent (SEQ ID NO: 7).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is an N-methylated leucine residue, $Xaa_{30}$ is a tryptophan residue, and $Xaa_{31}$ is absent (SEQ ID NO: 8).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is an isoleucine residue, $Xaa_{30}$ is a leucine residue, and $Xaa_{31}$ is a tryptophan residue (SEQ ID NO: 9).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is a leucine residue, $Xaa_{30}$ is an isoleucine residue, and $Xaa_{31}$ is absent (SEQ ID NO: 10).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is an isoleucine residue, and $Xaa_{31}$ is absent (SEQ ID NO: 11).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is an N-methylated leucine residue, $Xaa_{30}$ is an isoleucine residue, and $Xaa_{31}$ is absent (SEQ ID NO: 12).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is an isoleucine residue, $Xaa_{29}$ is a leucine residue, $Xaa_{30}$ is a tryptophan residue, and $Xaa_{31}$ is absent (SEQ ID NO: 13).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is an isoleucine residue, $Xaa_{29}$ is an isoleucine residue, $Xaa_{30}$ is a tryptophan residue, and $Xaa_{31}$ is absent (SEQ ID NO: 14).

In another embodiment, the present invention provides an isolated peptide comprising the amino acid sequence of SEQ ID NO: 1, wherein $Xaa_{12}$ is an alanine residue, $Xaa_{19}$ is a leucine residue, $Xaa_{28}$ is a lysine residue, $Xaa_{29}$ is a tryptophan residue, $Xaa_{30}$ is absent, and $Xaa_{31}$ is absent (SEQ ID NO: 15).

In one embodiment, $Xaa_{31}$ is absent. In another embodiment, $Xaa_{30}$ and $Xaa_{31}$ are both absent.

In another embodiment, the peptide of the invention is 31 amino acid residues in length. In another embodiment, the peptide of the invention is 30 amino acid residues in length. In another embodiment, the peptide of the invention is 29 amino acid residues in length. In another embodiment, the peptide of the invention is more than 31 amino acid residues in length, e.g. 32, 33, 34, 35, 36, 37, 38, 39, 40, or 41 residues in length. In this embodiment, the peptide contains additional amino acids at the C-terminus and/or N-terminus of the sequences described herein.

In another embodiment, the peptide of the invention consists of the amino acid sequence of SEQ ID NO: 1, wherein the amino acid sequence is 29, 30 or 31 amino acid residues in length.

In one embodiment, at least one of $Xaa_{12}$, $Xaa_{19}$, $Xaa_{28}$, $Xaa_{29}$ and $Xaa_{30}$ is a canonical amino acid residue. A "canonical" amino acid is an amino acid listed in the following table.

| Amino Acid | 3 Letter Code | 1 Letter Code |
|---|---|---|
| Alanine | Ala | A |
| Glutamine | Gln | Q |
| Leucine | Leu | L |
| Serine | Ser | S |
| Arginine | Arg | R |
| Glutamic Acid/Glutamate | Glu | E |
| Lysine | Lys | K |
| Threonine | Thr | T |
| Asparagine | Asn | N |
| Glycine | Gly | G |
| Methionine | Met | M |
| Tryptophan | Trp | W |
| Aspartic Acid/Aspartate | Asp | D |
| Histidine | His | H |
| Phenylalanine | Phe | F |
| Tyrosine | Tyr | Y |
| Cysteine | Cys | C |
| Isoleucine | Ile | I |
| Proline | Pro | P |
| Valine | Val | V |

As used herein, the terms “canonical amino acid” and “natural amino acid” are synonymous. As also used herein, the terms “canonical amino acid residue” and “natural amino acid residue” are synonymous.

In another embodiment, at least one of $Xaa_{12}$, $Xaa_{19}$, $Xaa_{28}$, $Xaa_{29}$ and $Xaa_{30}$ is a modified canonical amino acid residue, which is a canonical amino acid residue as defined above to which a chemical moiety, e.g., an amino group or a methyl group, is covalently attached to the canonical amino acid residue. Such chemical moieties may be one or more moieties known in the art for amino acid modification, e.g. $C_1$-$C_4$ alkyl groups, halogens like F or Cl, amino groups, $C_1$-$C_4$ amide groups, $C_1$-$C_4$ ether or ester groups, or any combination thereof. In a particular embodiment, there is only one chemical moiety present, typically an amino group or a $C_1$-$C_4$ alkyl group. Examples for modified canonical residues are N-Me-Leu (nml; this is also a non-canonical amino acid residue, see below), α-Me-Leu (aml) and Trp-$NH_2$. In specific embodiments, such modified canonical amino acid residue is a canonical amino acid residue to which a methyl group is covalently attached, e.g. nml or aml. The latter modified amino acids can, e.g., be present at position $Xaa_{29}$.

In another embodiment, at least one of $Xaa_{12}$, $Xaa_{19}$, $Xaa_{28}$, $Xaa_{29}$ and $Xaa_{30}$ is a non-canonical amino acid residue. As used herein, a “non-canonical amino acid residue” is an amino acid residue in D- or L-form that is not among the 20 canonical amino acids in the Table above. Non-limiting examples of non-canonical amino acid residues include β-amino acids, homoamino acids, cyclic amino acids and amino acids with derivatized side chains. Examples include (in the L-form or D-form): citrulline (Cit), homocitrulline (hCit), N-methylcitrulline (NMeCit), N-methylhomocitrulline (NMeHoCit), ornithine (Orn or O), N-Methylomithine (NMeOrn), sarcosine (Sar), homolysine (hK or Hlys), homoarginine (hR or hArg), homoglutamine (hQ), N-methylarginine (NMeR), N-methylleucine (NmeL; nml), N-methylhomolysine (NMeHoK), N-methylglutamine (NMeQ), norleucine (Nle), norvaline (Nva), 1,2,3,4-tetrahydroisoquinoline (Tic), nitrophenylalanine (nitrophe), aminophenylalanine (aminophe), benzylphenyalanine (benzylphe), γ-carboxyglutamic acid (γ-carboxyglu), hydroxyproline (hydroxypro), p-carboxyl-phenylalanine (Cpa), α-aminoadipic acid (Aad), acetylarginine (acetylarg), α,β-diaminopropionoic acid (Dpr), α,γ-diaminobutyric acid (Dab), diaminopropionic acid (Dap), β-(1-Naphthyl)-alanine (1Nal), β-(2-Naphthyl)-alanine (2Nal), cyclohexylalanine (Cha), 4-methyl-phenylalanine (MePhe), β,β-diphenyl-alanine (BiPhA), aminobutyric acid (Abu), 4-phenyl-phenylalanine (4Bip), α-amino-isobutyric acid (Aib), and derivatized forms of any of these as described herein. Nomenclature and symbolism for amino acids and peptides by the UPAC-IUB Joint Commission on Biochemical Nomenclature (JCBN) have been published in the following documents: *Biochem. J.* 219: 345-373 (1984); *Eur. J. Biochem.* 138: 9-37 (1984); *Internat. J. Pept. Prot. Res.* 24, 84 (1984); *J. Biol. Chem.* 260: 14-42 (1985); and *Amino Acids and Peptides* 16: 387-410 (1985).

In one embodiment, an amino acid residue is an “acidic residue,” which is an amino acid residue in D- or L-form having a sidechain comprising an acidic group. Exemplary acidic residues include aspartate (D) residues and glutamate (E) residues.

In another embodiment, an amino acid residue is an “amide residue,” which is an amino acid residue in D- or L-form having a sidechain comprising an amide derivative of an acidic group. Exemplary residues include asparagine (N) residues and a glutamine (Q) residues.

In another embodiment, an amino acid residue is an “aromatic residue,” which is an amino acid residue in D- or L-form having a sidechain comprising an aromatic group. Exemplary aromatic residues include phenylalanine (F) residues, tyrosine (Y) residues, and tryptophan (W) residues.

In another embodiment, an amino acid residue is a “basic residue,” which is an amino acid residue in D- or L-form having a sidechain comprising a basic group. Exemplary basic residues include histidine (H) residues, lysine (K) residues, arginine (R) residues, N-methyl-arginine residues, ω-aminoarginine residues, α-methyl-arginine residues, 1-methyl-histidine residues, 3-methyl-histidine residues, and homoarginine (hR) residues.

In another embodiment, an amino acid residue is a “hydrophilic residue,” which is an amino acid residue in D- or L-form having a sidechain comprising a polar group. Exemplary hydrophilic residues include histidine (H) residues, cysteine (C) residues, serine (S) residues, threonine (T) residues, asparagine (N) residues, glutamine (Q) residues, aspartate (D) residues, glutamate (E) residues, lysine (K) residues, proline (P) residues, and citrulline (Cit) residues.

In another embodiment, the amino acid residue is an amino acid residue in D- or L-form having a sidechain that lacks an acidic, basic, or aromatic group. Such amino acid residues include methionine (M) residues, glycine (G) residues, alanine (A) residues, valine (V) residues, isoleucine (I) residues, leucine (L) residues and norleucine (Nle) residues.

In another embodiment, an amino acid residue is a “neutral residue,” which is an amino acid residue in D- or L-form having a sidechain that lacks a basic, acidic, or polar group. Exemplary neutral polar amino acid residues include alanine (A) residues, valine (V) residues, leucine (L) residues, isoleucine (I) residues, proline (P) residues, tryptophan (W) residues, and phenylalanine (F) residues.

In another embodiment, an amino acid residue is a “hydrophobic residue,” which is a hydrophobic amino acid residue in D- or L-form having a sidechain that lacks a basic or an acidic groups. Exemplary hydrophobic amino acid residues include alanine (A) residues, valine (V) residues, leucine residues, phenylalanine (F) residues, threonine (T) residues, glycine (G) residues and tyrosine (Y) residues.

As used herein, the term “amino” or “amino group” refers to $—NH_2$.

In another embodiment, at least one of $Xaa_{12}$, $Xaa_{19}$, $Xaa_{28}$, $Xaa_{29}$ and $Xaa_{30}$ is a modified non-canonical amino acid residue, which is a non-canonical amino acid residue to which a chemical moiety, e.g., an amino group or a methyl group, is covalently attached to the non-canonical amino acid residue. Such chemical moieties may be one or more moieties known in the art for amino acid modification, e.g. $C_1$-$C_4$ alkyl groups, halogens like F or Cl, amino groups, $C_1$-$C_4$ amide groups, $C_1$-$C_4$ ether or ester groups, or any combination thereof. In a particular embodiment, there is only one chemical moiety present, typically an amino group or a $C_1$-$C_4$ alkyl group.

In one embodiment, at least one of $Xaa_{12}$, $Xaa_{19}$, $Xaa_{28}$, $Xaa_{29}$ and $Xaa_{30}$ is a hydrophilic amino acid residue. In another embodiment, at least one of $Xaa_{12}$, $Xaa_{19}$, $Xaa_{28}$, $Xaa_{29}$ and $Xaa_{30}$ is a hydrophobic amino acid residue. In another embodiment, at least one of $Xaa_{12}$, $Xaa_{19}$, $Xaa_{28}$, $Xaa_{29}$ and $Xaa_{30}$ is a neutral amino acid residue.

In another embodiment, $Xaa_{12}$ is a neutral residue or an acidic residue. In another embodiment, $Xaa_{19}$ is a residue which lacks acidic, basic or aromatic groups, or a neutral residue. In another embodiment, $Xaa_{28}$ is a hydrophilic or neutral residue. In another embodiment, $Xaa_{29}$ is a neutral residue. In another embodiment, $Xaa_{30}$ is a neutral or aromatic residue. In another embodiment, $Xaa_{31}$ is an aromatic residue. In another embodiment, a combination of these definitions for $Xaa_{12}$, $Xaa_{19}$, $Xaa_{28}$, $Xaa_{29}$, $Xaa_{30}$ and Xaa31 is realized. For example, in one embodiment, $Xaa_{12}$ is a neutral or acidic residue, e.g. alanine or glutamate, and $Xaa_{19}$ is a residue which lacks acidic, basic or aromatic groups, or a neutral residue, e.g. leucine or methionine.

In another embodiment, $Xaa_{12}$ is an alanine residue. In another embodiment, $Xaa_{19}$ is a leucine residue.

In another embodiment, $Xaa_{12}$ is an alanine residue and $Xaa_{19}$ is a leucine residue.

In another embodiment, $Xaa_{12}$ is an alanine residue, $Xaa_{19}$ is a leucine residue; $Xaa_{28}$ is any natural or modified amino acid residue, $Xaa_{29}$ is any natural or modified amino acid residue, and $Xaa_{30}$ is any natural or modified amino acid residue or is absent.

In another embodiment, $Xaa_{12}$ is a glutamate residue, $Xaa_{19}$ is a methionine residue, $Xaa_{28}$ is a lysine residue, $Xaa_{29}$ is a leucine residue, $Xaa_{30}$ is a tryptophan residue modified with an amino group, and $Xaa_{31}$ is absent (SEQ ID NO: 2).

In another embodiment, $Xaa_{12}$ is an alanine residue, $Xaa_{19}$ is a methionine residue, $Xaa_{28}$ is a lysine residue, $Xaa_{29}$ is a leucine residue, $Xaa_{30}$ is a tryptophan residue, and $Xaa_{31}$ is absent (SEQ ID NO: 3).

In another embodiment, $Xaa_{12}$ is a glutamate residue, $Xaa_{19}$ is a leucine residue, $Xaa_{28}$ is a lysine residue, $Xaa_{29}$ is a leucine residue, $Xaa_{30}$ is a tryptophan residue, and $Xaa_{31}$ is absent (SEQ ID NO: 4).

In another embodiment, $Xaa_{12}$ is a glutamate residue, $Xaa_{19}$ is a methionine residue, $Xaa_{28}$ is an isoleucine residue, $Xaa_{29}$ is an isoleucine residue, $Xaa_{30}$ is absent, and $Xaa_{31}$ is absent (SEQ ID NO: 5).

In another embodiment, $Xaa_{12}$ is an alanine residue, $Xaa_{19}$ is a leucine residue, $Xaa_{28}$ is a lysine residue, $Xaa_{29}$ is a leucine residue, $Xaa_{30}$ is a tryptophan residue, and $Xaa_{31}$ is absent (SEQ ID NO: 6).

In another embodiment, $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is a tryptophan residue, and $Xaa_{31}$ is absent (SEQ ID NO: 7).

In another embodiment, $Xaa_{12}$ is an alanine residue, $Xaa_{19}$ is a leucine residue, $Xaa_{28}$ is a lysine residue, $Xaa_{29}$ is an N-methylated leucine residue, $Xaa_{30}$ is a tryptophan residue, and $Xaa_{31}$ is absent (SEQ ID NO: 8).

In another embodiment, $Xaa_{12}$ is an alanine residue, $Xaa_{19}$ is a leucine residue, $Xaa_{28}$ is a lysine residue, $Xaa_{29}$ is an isoleucine residue, $Xaa_{30}$ is a leucine residue, and $Xaa_{31}$ is a tryptophan residue (SEQ ID NO: 9).

In another embodiment, $Xaa_{12}$ is an alanine residue, $Xaa_{19}$ is a leucine residue, $Xaa_{28}$ is a lysine residue, $Xaa_{29}$ is a leucine residue, $Xaa_{30}$ is an isoleucine residue, and $Xaa_{31}$ is absent (SEQ ID NO: 10).

In another embodiment, $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is an isoleucine residue, and $Xaa_{31}$ is absent (SEQ ID NO: 11).

In another embodiment, $Xaa_{12}$ is an alanine residue, $Xaa_{19}$ is a leucine residue, $Xaa_{28}$ is a lysine residue, $Xaa_{29}$ is an N-methylated leucine residue, $Xaa_{30}$ is an isoleucine residue, and $Xaa_{31}$ is absent (SEQ ID NO: 12).

In another embodiment, $Xaa_{12}$ is an alanine residue, $Xaa_{19}$ is a leucine residue, $Xaa_{28}$ is an isoleucine residue, $Xaa_{29}$ is a leucine residue, $Xaa_{30}$ is a tryptophan residue, and $Xaa_{31}$ is absent (SEQ ID NO: 13).

In another embodiment, $Xaa_{12}$ is an alanine residue, $Xaa_{19}$ is a leucine residue, $Xaa_{28}$ is an isoleucine residue, $Xaa_{29}$ is an isoleucine residue, $Xaa_{30}$ is a tryptophan residue, and $Xaa_{31}$ is absent (SEQ ID NO: 14).

In another embodiment, $Xaa_{12}$ is an alanine residue, $Xaa_{19}$ is a leucine residue, $Xaa_{28}$ is a leucine residue, $Xaa_{29}$ is a tryptophan residue, $Xaa_{30}$ is absent, and $Xaa_{31}$ is absent (SEQ ID NO: 15).

In one embodiment, the peptide of the present invention does not comprise the amino acid sequence of ProTx II (SEQ ID NO: 16), PaTx I (SEQ ID NO: 17), JTx XII (SEQ ID NO: 18), GsAF I (SEQ ID NO: 19), JzTx V (SEQ ID NO: 20), VsTx II (SEQ ID NO: 21), GsAF II (SEQ ID NO: 22), GrTx I (SEQ ID NO: 23), or GsMTx II/PaTx II (SEQ ID NO: 24), SEQ ID NO: 25, SEQ ID NO: 26, SEQ ID NO: 27, SEQ ID NO: 28 or SEQ ID NO: 29.

In another embodiment, the peptide of the present invention does not comprise the amino acid sequence of a peptide disclosed in Smith, J. J. et al., *J. Biol. Chem.* 287: 12687-12697 (2007), i.e., the peptide of the invention does not comprise any of SEQ ID NOS: 25-29, and does not comprise any of the Y1A, Q3A, K4Q, W5A, M6A, W7A, T8A, D10A, S11A, E12A, R13Q, K14A E17A, M19A, V20A, R22A, L23A, W24L, K26Q, K27Q, K28A, L29A or W30A mutations of ProTx II (SEQ ID NO: 16).

In another embodiment, a peptide of the present invention does not comprise the amino acid sequence of SEQ ID NO: 12 and SEQ ID NO: 15.

In one embodiment, if $Xaa_{12}$ in SEQ ID NO: 1 is an alanine residue and $Xaa_{31}$ is absent, then the amino acid sequence is not $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (SEQ ID NO: 25).

In another embodiment, if $Xaa_{19}$ in SEQ ID NO: 1 is an alanine residue and $Xaa_{31}$ is absent, then the amino acid sequence is not $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Ala_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (SEQ ID NO: 26).

In another embodiment, if $Xaa_{28}$ in SEQ ID NO: 1 is an alanine residue and $Xaa_{31}$ is absent, then the amino acid sequence is not $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Ala_{28}$-$Leu_{29}$-$Trp_{30}$-$Xaa_{31}$ (SEQ ID NO: 27).

In another embodiment, if $Xaa_{29}$ in SEQ ID NO: 1 is an alanine residue and $Xaa_{31}$ is absent, then the amino acid sequence is not $Tyr_1$-$Cys_2$-$Gln_3$-$Lys_4$-$Trp_5$-$Met_6$-$Trp_7$-$Thr_8$-

$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Ala_{29}$-$Trp_{30}$ (SEQ ID NO: 28);

In another embodiment, if $Xaa_{30}$ in SEQ ID NO: 1 is an alanine residue and $Xaa_{31}$ is absent, then the amino acid sequence is not $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Ala_{30}$ (SEQ ID NO: 29).

In another embodiment, the isolated peptide is not one in which (a) one of $Xaa_{12}$, $Xaa_{19}$, $Xaa_{28}$, $Xaa_{29}$, or $Xaa_{30}$ is an alanine residue, and (b) the amino acid residues at the other variable Xaa positions are the same amino acid residues as in ProTx II (SEQ ID NO: 16).

In one embodiment, the isolated peptide is a recombinantly expressed peptide. In another embodiment, the isolated peptide is a chemically synthesized peptide.

The present invention also provides a composition comprising an isolated peptide of SEQ ID NO: 1. In one embodiment, the composition is a sterile composition.

The present invention also provides a container comprising an isolated peptide of SEQ ID NO: 1. In one embodiment, the container is a vial. In another embodiment, the container is an intravenous fluid delivery container, e.g., a bag, a length of tubing, or a cartridge, each of which can be adapted for use with a mechanized analgesic delivery system, such as a pump.

The present invention also provides a pharmaceutical composition comprising an isolated peptide comprising the amino acid sequence of SEQ ID NO: 1 or a salt, prodrug or solvate thereof, and a pharmaceutically acceptable carrier or diluent. The present invention may further comprise a sterile container comprising the pharmaceutical composition of the present invention.

The present invention also provides an article of manufacture comprising a plurality of containers, each of which contains a pharmaceutical composition of the present invention.

The present invention also provides a polynucleotide molecule comprising a nucleotide sequence encoding the amino acid sequence of SEQ ID NO: 1. In cases where the amino acid sequence contains non-canonical amino acids or modified amino acids, the nucleotide sequence encodes its natural occurring counterpart. In one embodiment, the polynucleotide molecule is a deoxyribonucleic acid (DNA), such as cDNA. In another embodiment, the polynucleotide molecule is a ribonucleic acid (RNA), such as messenger RNA (mRNA).

The present invention also provides a recombinant vector comprising a polynucleotide molecule of the invention. In one embodiment, the vector is an expression vector. In a preferred embodiment, the recombinant vector comprises the polynucleotide molecule of the invention in operative association with one or more control elements necessary to enable the expression of the polynucleotide molecule under appropriate conditions.

The present invention also provides a host cell comprising a vector of the present invention. As used herein, the term "host cell" refers to either a single host cell or a plurality of host cells. In one embodiment, the host cell is a eukaryotic host cell, e.g., a mammalian cell, a plant cell, a yeast cell or an insect cell. In one embodiment, the mammalian cell is a human cell or a cell of human origin. In another embodiment, the host cell is a prokaryotic cell. In one embodiment, the prokaryotic cell is a bacterial cell.

The present invention also provides a recombinant method of making a peptide comprising the amino acid of SEQ ID NO: 1, said method comprising culturing a host cell comprising a polynucleotide molecule of the present invention in culture medium and under conditions suitable to induce expression of the peptide; and then isolating the peptide from the host cell or culture medium.

The invention disclosed herein also encompasses any of the disclosed peptides being isotopically-labelled (i.e., radiolabeled) by having one or more atoms thereof replaced by an atom having a different atomic mass or mass number. Examples of isotopes that can be incorporated into the disclosed peptides of the present invention include isotopes of hydrogen, carbon, nitrogen, oxygen, phosphorous, fluorine and chlorine, such as 2H, $^{3}H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively, and preferably $^{3}H$, $^{11}C$, and $^{14}C$. Isotopically-labeled peptides of SEQ ID NO: 1 can be prepared by methods known in the art in view of this disclosure.

The invention disclosed herein is also intended to encompass peptides of the present invention that have been fluorescently labeled or labeled with Europium or a Europium-based label.

The present invention also provides the use of any of the radiolabeled or fluorescently labeled peptides of the invention as detectably labeled ligands to bind to the sodium channel. One use of such labeled peptides is the characterization of specific receptor binding. Another use of such labeled peptides is as an alternative to animal testing for the evaluation of chemical structure-activity relationships. For example, the receptor assay can be performed at a fixed concentration of a labeled peptide of SEQ ID NO: 1 and at increasing concentrations of a candidate peptide in a competition assay. For example, a radiolabeled peptide such as a tritiated peptide of SEQ ID NO: 1 can be prepared by introducing tritium into the particular peptide, for example, by catalytic dehalogenation with tritium. This method may include reacting a suitably halogen-substituted precursor of the peptide with tritium gas in the presence of a suitable catalyst, for example Pd/C, in the presence or absence of a base. Other suitable methods for preparing tritiated peptides can be found in Filer, *Isotopes in the Physical and Biomedical Sciences, Vol.* 1, *Labeled Compounds* (*Part A*), Chapter 6 (1987). $^{14}C$-labeled peptides can be prepared by employing starting materials having a $^{14}C$ carbon.

The invention disclosed herein also encompasses the preparation and use of salts of the disclosed peptides, including all pharmaceutically acceptable salts of the disclosed peptides. Examples of pharmaceutically acceptable addition salts include inorganic and organic acid addition salts and basic salts. The pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate or the like.

Acid addition salts can be formed by mixing a solution of the particular peptide of the invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, or the like. Basic salts can be formed by mixing a solution of the peptide of SEQ ID NO: 1 with a solution of a pharmaceutically acceptable non-toxic base such as sodium hydroxide, potassium hydroxide, choline hydroxide, sodium carbonate or the like.

The invention disclosed herein is also meant to encompass solvates of any of the disclosed peptides. Solvates typically do not significantly alter the physiological activity or toxicity of the peptides, and as such may function as pharmacological equivalents. The term "solvate" as used herein is a combination, physical association and/or solvation of a peptide of the invention with a solvent molecule such as, e.g. a disolvate, monosolvate or hemisolvate, where the ratio of solvent molecule to peptide is typically 2:1, 1:1 or 1:2, respectively. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. Peptides of the invention may be unsolvated, or may be solvated with a pharmaceutically acceptable solvent such as water, methanol, ethanol, and the like. One type of solvate is a hydrate. A "hydrate" relates to a particular subgroup of solvates where the solvent molecule is water. Methods for preparing solvates are generally known in the art. See, for example, M. Caira et al, *J. Pharmaceut. Sci.,* 93(3):601-611 (2004), which describes the preparation of solvates of fluconazole with ethyl acetate, and with water. Similar preparation of solvates, hemisolvates, hydrates, and the like are described by E. C. van Tonder et al., *AAPS Pharm. Sci. Tech.,* 5(1):Article 12 (2004), and A. L. Bingham et al., *Chem. Commun.:* 603-604 (2001). A typical, non-limiting, process of preparing a solvate would involve dissolving a peptide of the invention in a desired solvent (organic, water, or a mixture thereof) at temperatures above about 20° C. to about 25° C., then cooling the solution at a rate sufficient to form crystals, and isolating the crystals by known methods, e.g., filtration. Analytical techniques such as infrared spectroscopy can be used to confirm the presence of the solvent in a crystal of the solvate.

The present invention also provides N-terminal and C-terminal derivatives of the peptides of the invention. For example, the N-terminal amino acid residue and/or the C-terminal amino acid residue of the peptide can be derivatized with an amino acid residue or another chemical moiety. In one embodiment, the N-terminal amino acid residue and/or the C-terminal amino acid residue of the peptide is derivatized with another chemical moiety, i.e. a moiety which is not an amino acid. Non-limiting examples of moieties with which the N-terminal (first) amino acid can be derivatized include an alkyl group (such as $C_1$-$C_4$ alkyl), a methyl group, a carboxy group, an acetyl group, and a substituted acetyl group. Non-limiting examples of chemical moieties with which the C-terminal (last) amino acid can be derivatized include an alkyl group (such as $C_1$-$C_4$ alkyl, e.g. a methyl or ethyl group); an aryl group or aryl alkyl group, such as phenyl or benzyl; a halogen, such as a fluoro or chloro; an alkoxy group; and an amino group.

The present invention also provides a method for treating or preventing a disorder responsive to the blockade of sodium channels, and particularly the selective blockade of $Na_V1.7$ sodium channels, in a subject suffering from, or at risk of suffering from, the disorder, the method comprising administering to the subject an effective amount of a peptide of the invention.

In one embodiment, the present invention provides a method of treating pain (palliative treatment). In another embodiment, the present invention provides a method of preventing pain (pre-emptive treatment). In one embodiment, the type of pain treated is chronic pain. In another embodiment, the type of pain treated is acute pain. In another embodiment, the type of pain treated is neuropathic pain. In another embodiment, the type of pain treated is inflammatory pain. In another embodiment, the type of pain treated is surgical pain. In each instance, such method of treatment or prevention requires administering to a subject in need of such treatment or prevention an amount of a peptide of the invention that is therapeutically effective in achieving said result. In one embodiment, the amount of such peptide is the amount that is effective to substantially block sodium channels in vivo.

Chronic pain includes, but is not limited to, inflammatory pain, neuropathic pain, postoperative pain, cancer pain, osteoarthritis pain associated with metastatic cancer, trigeminal neuralgia, acute herpetic and postherpetic neuralgia, diabetic neuropathy, causalgia, brachial plexus avulsion, occipital neuralgia, reflex sympathetic dystrophy, fibromyalgia, gout, phantom limb pain, burn pain, and other forms of neuralgia, neuropathic, and idiopathic pain syndromes.

The methods of the present invention may be used to treat or prevent chronic somatic pain, which generally results from inflammatory responses to tissue injury such as nerve entrapment, surgical procedures, cancer or arthritis (Brower, *Nature Biotechnology* 2000; 18: 387-391).

Inflammatory pain includes, but is not limited to, pain associated with osteoarthritis and rheumatoid arthritis.

The methods of the present invention may be used to treat or prevent chronic neuropathic pain, which is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. Chronic pain is different from acute pain in that patients suffering from chronic pain suffer the abnormal pain sensations that can be described as spontaneous pain, continuous superficial burning and/or deep aching pain. The pain can be evoked by heat-, cold-, and mechano-hyperalgesia or by heat-, cold-, or mechano-allodynia.

The methods of the present invention may be used to treat or prevent neuropathic pain, which can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can also cause nerve injury. Neuropathic pain includes but is not limited to pain caused by nerve injury such as, for example, the pain from which diabetics suffer.

The methods of the present invention may also be used to treat or prevent epilepsy, seizures, epilepsy with febrile seizures, epilepsy with benign familial neonatal infantile seizures, inherited pain disorders, e.g., primary erythermalgia and paroxysmal extreme pain disorder, familial hemiplegic migraine, movement disorder, psychiatric disorders (such as autism, cerebeller atrophy, ataxia, and mental retardation/neurodegeneration), global or focal ischemia, myotonia, a movement disorder, erythermalgia, cardiac arrhythmias or other conduction disorders, including supraventricular tachycardia, ventricular tachycardia, symptomatic ventricular premature beats, and prevention of ventricular fibrillationventricular fibrillation, and to provide local anesthesia.

In one embodiment, the subject being treated by a method of the present invention is a mammal. In another embodiment, the mammal is a human, or other primate (e.g., a chimpanzee, orangutan, gorilla, or lemur), or a canine (e.g., a dog, fox, wolf, or coyote), feline (e.g., a cat, lion, tiger, bobcat, leopard, cheetah, panther), equine (e.g., a horse, llama, alpaca, zebra, deer, moose, elk, mule or donkey), bovine (e.g., a cow, a bull, a buffalo or a bison), or a pig, marine mammal (e.g., a seal, walrus, otter, sea lion, manatee, dolphin, porpoise or whale), rodent (e.g., a rat, a mouse, ferret or guinea pig), or any other mammal.

In one embodiment, a peptide of the invention is administered to the subject by any suitable route of administration, including by one or more of the oral, buccal, mucosal, sublingual, parenteral, subcutaneous, intramuscular, intraperitoneal, intrathecal, intranasal, inhalation, transdermal, rectal or vaginal routes of administration.

The present invention is also directed to the use of a peptide of the invention in the manufacture of a medicament for modulating sodium channels, especially $Na_v1.7$ sodium channels, in an in vitro or in vivo system.

The present invention is also directed to the use of a peptide of the invention in the manufacture of a medicament for treating a disorder or providing preemptive or palliative treatment of a disorder that is responsive to the blockade of sodium channels (e.g., any of the disorders listed above) in a subject suffering from said disorder. In one embodiment, the disorder is responsive to the selective blockade of $Na_v1.7$ sodium channels.

Synthesis of Peptides

The peptides of the invention can be synthesized using peptide synthesis methodologies, in which amino acids are linked by peptide bonds, and other chemical synthetic procedures, as known in the art and in view of this disclosure. For example, see Pennington, M. W., Ed., "Peptide Synthesis Protocols," in *Methods in Molecular Biology* 35, Humana Press; and Atherton, E. and Sheppard, R. C., "*Solid Phase peptide synthesis: a practical approach,*" IRL Press. (1989). Non-limiting examples of synthetic methods are liquid-phase synthesis and solid-phase synthesis. Non-limiting examples of solid-phase synthesis are Fmoc solid-phase synthesis (e.g., the syntheses used in the Examples), and t-boc solid phase synthesis.

For forming cystine bridges, any conventional method can be used, e.g. an oxidation method using GSSG like the method described in the examples. Typically, there are 3 cystine bridges present in the peptide of the invention. They typically have the connectivity $C_2$ to $C_{16}$, $C_9$ to $C_{21}$ and $C_{15}$ to $C_{25}$.

Testing of Peptides

Representative peptides of the invention can be assessed by electrophysiological assays testing for sodium channel activity. One aspect of the present invention is based on the use of the peptides herein described as sodium channel blockers. In one aspect of the present invention, it has been found that certain peptides show selectivity as $Na_v1.7$ sodium channel blockers. Based upon this property, these peptides are considered useful in treating pain.

More specifically, the present invention is directed to peptides that are blockers of sodium channels. In one embodiment, peptides having preferred sodium channel blocking properties exhibit an $IC_{50}$ of about 100 μM or less in one or more of the sodium electrophysiological assays described herein, or an $IC_{50}$ of 10 μM or less, or an $IC_{50}$ of about 6 μM or less, or an $IC_{50}$ of about 1.0 μM or less, or an $IC_{50}$ of about 500 nM or less, or an $IC_{50}$ of about 100 nM or less.

Peptides of the invention can be tested for their sodium channel blocking activity using electrophysiological assays known in the art, such as the assay disclosed herein. For example, see Clare, J. J. et al., *Drug Discovery Today* 5: 506-520 (2000).

In one embodiment, peptides useful in the present invention are those represented by SEQ ID NO: 1 that exhibit selectivity for $Na_v1.7$ sodium channels over $Na_v1.2$ sodium channels in electrophysiological assays described herein. The phrase "selectivity for $Na_v1.7$ sodium channels over $Na_v1.2$ sodium channels" is used herein to mean that the ratio of an $IC_{50}$ for $Na_v1.7$ sodium channel blocking activity for a peptide of the invention over an $IC_{50}$ for $Na_v1.2$ sodium channel blocking activity for the same peptide is less than 1, i.e., $Na_v1.7\ IC_{50}/Na_v1.2\ IC_{50}<1$. Preferably, a peptide of SEQ ID NO: 1 exhibits an $Na_v1.7\ IC_{50}/Na_v1.2\ IC_{50}$ ratio of about 1/2, 1/3, 1/4, 1/5, 1//6, 1/7, 1/8, 1/9, 1/10, 1/15, 1/20, 1/25, 1/30, 1/35, 1/40, 1/45, 1/50, 1/55, 1/60, 1/65, 1/70, 1/75, 1/80, 1/85, 1/90, 1/95, 1/100, 1/125, 1/150, 1/175, 1/200, 1/225, 1/250, 1/275, 1/300, 1/325, 1/350, 1/375, 1/400, 1/425, 1/450, 1/475 or 1/500 or less.

In Vitro Assay Protocols:

FLIPR® Assays:

Recombinant $Na_v1.7$ Cell Line:

In vitro assays were performed in a recombinant cell line expressing cDNA encoding the alpha subunit ($Na_v1.7$, SCN9a, PN1, NE) of human $Na_v1.7$ (Accession No. NM_002977). The cell line was provided by investigators at Yale University (Cummins et al, *J. Neurosci.* 18(23): 9607-9619 (1998)). For dominant selection of the $Na_v1.7$-expressing clones, the expression plasmid co-expressed the neomycin resistance gene. The cell line was constructed in the human embryonic kidney cell line, HEK293, under the influence of the CMV major late promoter, and stable clones were selected using limiting dilution cloning and antibiotic selection using the neomycin analogue, G418. Recombinant beta and gamma subunits were not introduced into this cell line. Additional cell lines expressing recombinant $Na_v1.7$ cloned from other species can also be used, alone or in combination with various beta subunits, gamma subunits or chaperones.

Non-recombinant Cell Lines Expressing Native $Na_v1.7$:

Alternatively, in vitro assays can be performed in a cell line expressing native, non-recombinant $Na_v1.7$, such as the ND7 mouse neuroblastoma X rat dorsal root ganglion (DRG) hybrid cell line ND7/23, available from the European Cell Culture Collection (Cat. No. 92090903, Salisbury, Wiltshire, United Kingdom). The assays can also be performed in other cell lines expressing native, non-recombinant $Na_v1.7$ from various species, or in cultures of fresh or preserved sensory neurons, such as dorsal root ganglion (DRG) cells, isolated from various species. Primary screens or counter-screens of other voltage-gated sodium channels can also be performed, and the cell lines can be constructed using methods known in the art, purchased from collaborators or commercial establishments, and they can express either recombinant or native channels. The primary counter-screen is for one of the central neuronal sodium channels, $Na_v1.2$ (rBIIa), expressed in HEK293 host cells (Ilyin et al., *Br. J. Pharmacol.* 144:801-812 (2005)). Pharmacological profiling for these counter-screens is carried out under conditions similar to the primary or alternative $Na_v1.7$ assays described below.

Cell Maintenance:

Unless otherwise noted, cell culture reagents were purchased from Mediatech of Herndon, Va. The recombinant $Na_v1.7$/HEK293 cells were routinely cultured in growth medium consisting of Dulbecco's minimum essential medium containing 10% fetal bovine serum (FBS, Hyclone, Thermo Fisher Scientific, Logan, Utah), 100 U/mL penicillin, 100 μg/mL streptomycin, 2-4 mM L-glutamine, and 500 mg/mL G418. For natural, non-recombinant cell lines, the selective antibiotic was omitted, and additional media formulations can be applied as needed.

Assay Buffer:

The assay buffer was formulated by removing 120 mL from a 1 L bottle of fresh, sterile $dH_2O$ (Mediatech, Herndon, Va.) and adding 100 mL of 10×HBSS that does not contain $Ca^{++}$ or $Mg^{++}$ (Gibco, Invitrogen, Grand Island, N.Y.) followed by 20 mL of 1.0 M Hepes, pH 7.3 (Fisher Scientific, BP299-100). The final buffer consisted of 20 mM Hepes, pH 7.3, 1.261 mM $CaCl_2$, 0.493 mM $MgCl_2$, 0.407 mM $Mg(SO)_4$, 5.33 mM KCl, 0.441 mM $KH_2PO_4$, 137 mM NaCl, 0.336 mM $Na_2HPO_4$ and 0.556 mM D-glucose (Hanks et al., *Proc. Soc. Exp. Biol. Med.* 71:196 (1949)), and the simple formulation was typically the basic buffer throughout the assay (i.e., all wash and addition steps).

CoroNa™ Green AM $Na^+$ Dye for Primary Fluorescence Assay:

The fluorescence indicator used in the primary fluorescence assay was the cell permeant version of CoroNa™ Green (Invitrogen, Molecular Probes, Eugene, Oreg.), a dye that emits light in the fluorescence range (Harootunian et al., *J. Biol. Chem.* 264(32):19458-19467 (1989)). The intensity of this emission, but not the wavelength range, is increased when the dye is exposed to $Na^+$ ions, which it can bind with partial selectivity. Cells expressing $Na_v1.7$ or other sodium channels were loaded with the CoroNa™ Green dye immediately in advance of the fluorescence assay, and then, after agonist stimulation, the mobilization of $Na^+$ ions was detected as the $Na^+$ ions flowed from the extracellular fluid into the cytoplasm through the activated sodium channel pores. The dye was stored in the dark as a lyophilized powder, and then an aliquot was dissolved immediately before the cell loading procedure, according to the instructions of the manufacturer to a stock concentration of 10 mM in DMSO. It was then diluted in the assay buffer to a 4× concentrated working solution, so that the final concentration of dye in the cell loading buffer was 5 μM.

Membrane Potential Dye for Alternative Fluorescence Assays:

A fluorescence indicator that can be used in alternative fluorescence assays is the blue version membrane potential dye (MDS, Molecular Devices, Sunnyvale, Calif.), a dye that detects changes in molecules following a change in membrane potential. An increase in fluorescence is expected if agonist stimulation provokes a change in membrane potential. Cells expressing $Na_v1.7$ or other sodium channels are incubated with the membrane potential dye 30-60 minutes before the fluorescence assay. In the case of the KCl pre-stimulation version of the assay, the dye and all other components are washed out immediately before the assay, and the dye is then replaced. In the version lacking KCl pre-stimulation, the dye remains on the cells and is not washed out or replaced. The dye is stored in the dark as a lyophilized powder, and then an aliquot is dissolved in assay buffer to form a 20×-concentrated stock solution that can be used for several weeks.

Agonists:

In the fluorescence assays, two agonists were used in combination, namely 1) veratridine, and 2) the venom from the yellow scorpion, *Leiurus quinquestriatus hebraeus*. Veratridine is an alkaloid small molecule that facilitates the capture of channel openings by inhibiting inactivation, and the scorpion venom is a natural preparation that includes peptide toxins selective for different subsets of voltage-gated sodium channels. These scorpion toxins inhibit the fast inactivation of their cognate target channels. Stock solutions of the agonists were prepared to 40 mM in DMSO (veratridine) and 1 mg/mL in $dH_2O$ (scorpion venom), and then diluted to make a 4× or 2× stock (depending on the particular assay) in assay buffer, the final concentration being 100 μM (veratridine) and 10 μg/mL (scorpion venom). Both of the agonists were purchased from Sigma Aldrich, St. Louis, Mo.

Test Compounds:

Test compounds were dissolved in DMSO to yield 10 mM stock solutions. The stock solutions were further diluted using DMSO in 1:3 serial dilution steps with 10 points (10,000 μM, 3,333 μM, 1,111 μM, 370 μM, 123 μM, 41 μM, 14 μM, 4.6 μM, 1.5 μM and 0.5 μM). The stock solutions were further diluted in assay buffer (1:125) as 4× stock serial dilutions with a DMSO concentration of 0.8% (final [DMSO], in the assay, from the compounds component=0.2%), so that the compounds' final concentrations in the assay were 20 μM, 6.7 μm, 2.2 μM, 0.74 μM, 0.25 μM, 0.08 μM, 0.03 μM, 0.01 μM, 0.003 μM and 0.001 μM. If a particular test article appeared to be especially potent, then the concentration curve was adjusted, e.g., to 10-fold lower concentrations, in order to perform the dose-response in a more relevant concentration range. Compound dilutions were added during the dye-loading and pre-stimulation step, and then again during the fluorescence assay, early in the kinetic read. Compound dilutions were added in duplicate rows across the middle 80 wells of the 96-well plate, whereas the fully stimulated and the fully inhibited controls (positive and negative) were located in the top 4 side wells and the bottom 4 side wells, respectively, on the left and right sides of the assay plate.

Data Analysis:

The data were analyzed according to methods known in the art or using the GraphPad® Prism 4.0 Program (available from GraphPad Software, San Diego, Calif.) to determine the $IC_{50}$ value for the test article. At least one standard reference compound was evaluated during each experiment.

FLIPR® or FLIPR$^{TETRA}$® Sodium Dye Assay with KCl and Test Article Pre-Incubation:

Cells were prepared by plating the recombinant HEK293 cells or other host cells expressing either recombinant or non-recombinant, native $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate was then incubated in growth media, with or without selective antibiotic, overnight at 37° C. at 5% $CO_2$, 95% humidity, in preparation for the assay. For counter-screens of other voltage-gated sodium channels, the procedure was very similar, though optimal densities of cells, media and subsequent assay components can be fine-tuned for the particular cell line or isoform.

The next day, at the start of the assay, the media was flicked from the cells and the wells were washed once with 50 μL/well assay buffer (1× Hank's balanced salt solution without sodium bicarbonate or phenol red, 20 mM Hepes, pH 7.3) and then pre-incubated with the test articles, CoroNa™ Green AM sodium dye (for cell loading) and KCl for re-polarization and synchronization of the channels in the entire population of cells. For this dye-loading and pre-stimulation step, the components were added as follows, immediately after the wash step: 1) the compound dilutions and controls were added as 4× concentrates in assay buffer at 50 μL/well; 2) CoroNa™ Green AM dye was diluted from the stock solution to 20 μM in assay buffer (4× concentrate) and added to the plate at 50 μL/well; and 3) a solution of 180 mM KCl (2×) was prepared by diluting a 2M stock solution into assay buffer and the solution was added to the cells at 100 μL/well. The cells were incubated at 25° C. in the dark for 30 min. before their fluorescence was measured.

The plates containing dye-loaded cells were then flicked to remove the pre-incubation components and washed once with 100 μL/well assay buffer. A 100 μL/well aliquot of assay buffer was added back to the plate, and the real-time assay was commenced. The fluorescence of cells was measured using a fluorescence plate reader (FLIPR$^{TETRA}$® or FLIPR384®, MDS, Molecular Devices, Sunnyvale, Calif.). Samples were excited by either a laser or a PMT light source (Excitation wavelength=470-495 nM) and the emissions were filtered (Emission wavelength=515-575 nM). The additions of compound and the channel activators in this cell-based, medium-to-high throughput assay were performed on the fluorescence plate reader and the results (expressed as relative fluorescence units) were captured by means of camera shots every 1-3 sec., then displayed in real-time and stored. Generally, there was a 15 sec. base line, with camera shots taken every 1.5 sec., then the test compounds were added, then another 120 sec. baseline was conducted, with camera shots taken every 3 sec.; and finally, the agonist solution (containing veratridine and scorpion venom) was added. The amplitude of fluorescence increase, resulting from the binding of $Na^+$ ions to the CoroNa™ Green dye, was captured for ~180 sec. thereafter. Results were expressed in relative fluorescence units (RFU) and can be determined by using the maximum signal during the latter part of the stimulation; or the maximum minus the minimum during the whole agonist stimulation period; or by taking the area under the curve for the whole stimulation period.

The assay can be performed as a screening assay as well as with the test articles present in standard amounts (e.g., 10 μM) in only one or two wells of a multi-well plate during the primary screen. Hits in this screen were typically profiled more exhaustively (multiple times), subjected to dose-response or competition assays and tested in counter screens against other voltage-gate sodium channels or other biologically relevant target molecules.

FLIPR® or FLIPR$^{TETRA}$® Membrane Potential Assay with KCl and Test Article Pre-Incubation: Cells are prepared by plating the recombinant HEK293 cells or other host cells expressing either recombinant or non-recombinant, native $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay (see, e.g., Benjamin et. al., *J. Biomol. Screen* 10(4):365-373 (2005)). For screens and counterscreens of other voltage-gated sodium channels, the assay protocol is similar, though optimal densities of cells, media and subsequent assay components can be fine-tuned for the particular cell line or sodium channel isoform being tested.

The next day, at the start of the assay, the media is flicked from the cells and the wells are washed once with 50 μL/well assay buffer (1× Hank's balanced salt solution without sodium bicarbonate or phenol red, 20 mM Hepes, pH 7.3) and then pre-incubated with the test articles, the membrane potential dye (for cell loading), and the KCl for re-polarization and synchronization of the channels in the entire population of cells. For this dye-loading and pre-stimulation step, the components are added as follows, immediately after the wash step: 1) first, the compound dilutions and controls are added as 4× concentrates in assay buffer at 50 μL/well; 2) membrane potential dye is diluted from the stock solution in assay buffer (4× concentrate) and added to the plate at 50 μL/well; and 3) a solution of 180 mM KCl (2×) is prepared by diluting a 2M stock solution into assay buffer and the solution added to the cells at 100 μL/well. The cells are incubated at 37° C. in the dark for 30-60 min. before their fluorescence is measured.

The plates containing dye-loaded cells are then flicked to remove the pre-incubation components and washed once with 50 μL/well assay buffer. A 50 μL/well aliquot of membrane potential dye is added back to the plate, and the real-time assay is commenced. The fluorescence of cells is measured using a fluorescence plate reader (FLIPR$^{TETRA}$® or FLIPR384®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first) and then the channel activators (later) in this are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec. Finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well with the test articles present in standard amounts (e.g., 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

FLIPR® or FLIPR$^{TETRA}$® Sodium Dye Assay without KCl and Test Article Pre-Incubation:

Cells are prepared by plating the recombinant HEK293 cells or other host cells expressing either recombinant or non-recombinant, native, $Na_v1.7$ alpha subunit, alone or in combination with various beta and gamma subunits at a density of ~40,000 cells/well into a 96-well black, clear-bottom, PDL-coated plate. The assay can be adapted to 384-well or 1,536-well format, if desired, using proportionately less cells and media. The plate is then incubated in growth media, with or without selective antibiotic, overnight at 37° C. at 5% $CO_2$, 95% humidity, in preparation for the assay. For counterscreens of other voltage-gated sodium channels, the procedure is very similar, though optimal densities of cells, media and subsequent assay components can be fine-tuned for the particular cell line or isoform.

The next day, at the start of the assay, the media is flicked from the cells and the wells washed once with 50 μL/well assay buffer (1× Hank's balanced salt solution without sodium bicarbonate or phenol red, 20 mM Hepes, pH 7.3). Membrane potential dye is then added to each well of the 96-well plate (50 μL/well), from a freshly diluted sample of the stock (now at 4× concentration) in the assay buffer. The cells are incubated at 37° C. in the dark for 30-60 min. before their fluorescence is measured.

In this standard membrane potential assay, the 96-well plate containing dye-loaded cells is then loaded directly onto the plate reader without aspirating the dye solution and without any further washing of the cells. The fluorescence of cells is measured using a fluorescence plate reader (FLIPR$^{TETRA}$® or FLIPR$^{384}$®, MDS, Molecular Devices, Sunnyvale, Calif.). Samples are excited by either a laser or a PMT light source (Excitation wavelength=510-545 nM) and the emissions are filtered (Emission wavelength=565-625 nM). The additions of the compounds (first, 50 μL/well from a 4× stock plate) and then the channel activators (later, 100 μL/well from a 2× stock solution) in this kinetic assay are performed on the fluorescence plate reader and the results, expressed as relative fluorescence units (RFU), are captured by means of camera shots every 1-3 sec., then displayed in real-time and stored. Generally, there is a 15 sec. base line, with camera shots taken every 1.5 sec., then the test compounds are added, then another 120 sec. baseline is conducted, with camera shots taken every 3 sec. Finally, the agonist solution (containing veratridine and scorpion venom) is added. The amplitude of fluorescence increase, resulting from the detection of membrane potential change, is captured for ~120 sec. thereafter. Results are expressed in relative fluorescence units (RFU) and can be determined by using the maximum signal during the latter part of the stimulation; or the maximum minus the minimum during the whole stimulation period; or by taking the area under the curve for the whole stimulation period.

The assay can be performed as a screening assay as well, with the test articles present in standard amounts (e.g. 10 μM) in only one or two wells of a multi-well plate during the primary screen. Hits in this screen are typically profiled more exhaustively (multiple times), subjected to dose-response or competition assays and tested in counter screens against other voltage-gate sodium channels or other biologically relevant target molecules.

Electrophysiology Assay

Cells:

The hNa$_v$1.7 expressing HEK-293 cells were plated on 35 mm culture dishes pre-coated with poly-D-lysine in standard DMEM culture media (Mediatech, Inc., Herndon, Va.) and incubated in a 5% $CO_2$ incubator at 37° C. Cultured cells were used approximately 12-48 hours after plating.

Electrophysiology:

On the day of experimentation, the 35 mm dish was placed on the stage of an inverted microscope equipped with a perfusion system that continuously perfuses the culture dish with fresh recording media. A gravity driven superfusion system was used to apply test solutions directly to the cell under evaluation. This system consists of an array of glass pipettes connected to a motorized horizontal translator. The outlet of the shooter was positioned approximately 100 μm from the cell of interest.

Whole cell currents were recorded using the whole-cell patch clamp configuration using an Axopatch 200B amplifier (Axon Instruments, Foster City Calif.), 1322A A/D converter (Axon Instruments) and pClamp software (v. 8; Axon Instruments) and stored on a personal computer. Gigaseals were formed and the whole-cell configuration was established in voltage clamp mode, and membrane currents generated by hNa$_v$1.7 were recorded in gap-free mode. Borosilicate glass pipettes have resistance values between 1.5 and 2.0 MΩ2 when filled with pipette solution and series resistance (<5 MΩ) was compensated 75-80%. Signals were sampled at 50 kHz and low pass filtered at 3 kHz.

The voltage clamp protocol to examine hNa$_v$1.7 currents was as follows. First, the standard current-voltage relationship was tested by pulsing the cell from the holding voltage ($V_h$) of −120 mV by a series of 5 msec long square-shaped test pulses incrementing in +10 mV steps over the membrane voltage range of −90 mV to +60 mV at the pace of stimulation of 0.5 Hz. This procedure determines the voltage that elicits the maximal current ($V_{max}$). Second, $V_h$ was re-set to −120 mV and a steady-state inactivation (SSIN) curve was taken by the standard double-pulse protocol: 100 ms depolarizing pre-pulse was incremented in steps of +10 mV (voltage range from −90 mV to 0 mV) immediately followed by the 5 ms long test pulse to −10 mV at the pace of stimulation of 0.2 Hz. This procedure determines the voltage of full inactivation ($V_{full}$). Third, the cell was repeatedly stimulated with the following protocol, first in the absence of the test compound then in its presence. The protocol consisted of depolarizing the cell from the holding potential of −120 mV to the $V_{full}$ value for 4.5 seconds then repolarizing the cell to the holding potential for 10 ms before applying the test pulse to the $V_{max}$ for 5 ms. The amount of inhibition produced by the test compound was determined by comparing the current amplitude elicited by the test pulse in the absence and presence of the compound.

Solutions and Chemicals:

For electrophysiological recordings the external solution was either standard, DMEM supplemented with 10 mM HEPES (pH adjusted to 7.34 with NaOH and the osmolarity adjusted to 320) or Tyrodes salt solution (Sigma, USA) supplemented with 10 mM HEPES (pH adjusted to 7.4 with NaOH; osmolarity=320). The internal pipette solution contained (in mM): NaCl (10), CsF (140), $CaCl_2$ (1), $MgCl_2$ (5), EGTA (11), HEPES (10: pH 7.4, 305 mOsm). Compounds were prepared first as series of stock solutions in DMSO and then dissolved in external solution; DMSO content in final dilutions did not exceed 0.3%. At this concentration, DMSO did not affect sodium currents. Vehicle solution used to establish base line was also contacting 0.3% DMSO.

Data Analysis:

Data was analyzed off-line using Clampfit software (pClamp, v. 8; Axon Instruments) and graphed using GraphPad Prizm (v. 4.0) software.

In vivo Assay for Pain

The peptides of the invention can be tested for their antinociceptive activity in the formalin model as described in Hunskaar et al., *J. Neurosci. Methods* 14: 69-76 (1985). Male Swiss Webster NIH mice (20-30 g; Harlan, San Diego, Calif.) can be used in all experiments. Food is withdrawn on the day of experiment. Mice are placed in Plexiglass jars for at least 1 hour to acclimate to the environment. Following the acclimation period, mice are weighed and given either the compound of interest administered i.p. or p.o., or the appropriate volume of vehicle (for example, 10% Tween-80 or 0.9% saline, and other pharmaceutically acceptable vehicles) as control. Fifteen minutes after the i.p. dosing, and 30 minutes after the p.o. dosing, mice are injected with formalin (20 μL of 5% formaldehyde solution in saline) into the dorsal surface of the right hind paw. Mice are transferred to the Plexiglass jars and monitored for the amount of time spent licking or biting the injected paw. Periods of licking and biting are recorded in 5-minute intervals for 1 hour after the formalin injection. All experiments are done in a blinded manner during the light cycle. The early phase of the formalin response is measured as licking/biting between 0-5 minutes, and the late phase is measured from 15-50 minutes. Differences between vehicle and drug treated groups can be analyzed by one-way analysis of variance (ANOVA). A P value<0.05 is considered significant. Peptides are considered to be efficacious for treating acute and chronic pain if they have activity in blocking both the early and second phase of formalin-induced paw-licking activity.

In Vivo Assays for Inflammatory or Neuropathic Pain

Test Animals:

Each experiment uses rats weighing between 200-260 g at the start of the experiment. The rats are group-housed and have free access to food and water at all times, except prior to oral administration of a test compound when food is removed for 16 hours before dosing. A control group acts as a comparison to rats treated with test peptides. The control group is administered the carrier as used for the test compound. The volume of carrier administered to the control group is the same as the volume of carrier and test compound administered to the test group.

Inflammatory Pain:

To assess the actions of test peptides on the treatment of inflammatory pain, the Freund's complete adjuvant ("FCA") model of inflammatory pain is used. FCA-induced inflammation of the rat hind paw is associated with the development of persistent inflammatory mechanical and thermal hyperalgesia and provides reliable prediction of the anti-hyperalgesic action of clinically useful analgesic drugs (Bartho et al., *Naunyn-Schmiedeberg's Archives of Pharmacol.* 342:666-670 (1990)). The left hind paw of each animal is administered a 50 μL, intraplantar injection of 50% FCA. 24-hour post-injection, each animal is assessed for response to noxious mechanical stimuli by determining the paw withdrawal threshold (PWT), or to noxious thermal stimuli by determining the paw withdrawal latency (PWL), as described below. Rats are then administered a single injection of either a test peptide or 30 mg/Kg of a positive control compound (indomethacin). Responses to noxious mechanical or thermal stimuli are then determined 1, 3, 5 and 24 hours post administration (admin). Percentage reversal of hyperalgesia for each animal is defined as:

$$\% \text{ reversal} = \frac{\begin{bmatrix} (\text{post administration } PWT \text{ or } PWL) - \\ (\text{pre-administration } PWT \text{ or } PWL) \end{bmatrix}}{\begin{bmatrix} (\text{baseline } PWT \text{ or } PWL) - \\ (\text{pre-administration } PWT \text{ or } PWL) \end{bmatrix}} \times 100$$

Neuropathic Pain:

To assess the actions of the test compounds for the treatment of neuropathic pain the Seltzer model or the Chung model can be used.

In the Seltzer model, the partial sciatic nerve ligation model of neuropathic pain is used to produce neuropathic hyperalgesia in rats (Seltzer et al., *Pain* 43:205-218 (1990)). Partial ligation of the left sciatic nerve is performed under isoflurane/$O_2$ inhalation anaesthesia. Following induction of anaesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ reversal} = \frac{\begin{bmatrix} (\text{post administration } PWT) - \\ (\text{pre-administration } PWT) \end{bmatrix}}{\begin{bmatrix} (\text{baseline } PWT) - \\ (\text{pre-administration } PWT) \end{bmatrix}} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is (are) isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is (are) not manipulated. Following surgery, animals are weighed, administered a subcutaneous (s.c.) injection of saline or ringers lactate, the wound area is dusted with antibiotic powder and they are kept on a warm pad until they recover from the anaesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a peptide to the left rear paw of the animal. The animals can also be assessed for response to noxious thermal stimuli or for tactile allodynia, as described below. The Chung model for neuropathic pain is described in Kim et al., *Pain* 50(3):355-363 (1992).

Tactile Allodynia:

Sensitivity to non-noxious mechanical stimuli can be measured in animals to assess tactile allodynia. Rats are transferred to an elevated testing cage with a wire mesh floor and allowed to acclimate for five to ten minutes. A series of von Frey monofilaments are applied to the plantar surface of the hindpaw to determine the animal's withdrawal threshold. The first filament used possesses a buckling weight of 9.1 gms (0.96 log value) and is applied up to five times to see if it elicits a withdrawal response. If the animal has a withdrawal response, then the next lightest filament in the series would be applied up to five times to determine if it also could elicit a response. This procedure is repeated with subsequent lesser filaments until there is no response and the identity of the lightest filament that elicits a response is recorded. If the animal does not have a withdrawal response from the initial 9.1 gms filament, then subsequent filaments of increased weight are applied until a filament elicits a response and the identity of this filament is recorded. For each animal, three measurements are made at every time point to produce an average withdrawal threshold determination. Tests can be performed prior to, and at 1, 2, 4 and 24 hours post drug administration.

Mechanical Hyperalgesia:

Sensitivity to noxious mechanical stimuli can be measured in animals using the paw pressure test to assess mechanical hyperalgesia. In rats, hind paw withdrawal thresholds ("PWT"), measured in grams, in response to a noxious mechanical stimulus are determined using an analgesymeter (Model 7200, commercially available from Ugo Basile of Italy), as described in Stein (*Biochemistry & Behavior* 31: 451-455 (1988)). The rat's paw is placed on a small platform, and weight is applied in a graded manner up to a maximum of 250 grams. The endpoint is taken as the weight at which the paw is completely withdrawn. PWT is determined once for each rat at each time point. PWT can be measured only in the injured paw, or in both injured and non-injured paws. In one non-limiting embodiment, mechanical hyperalgesia associated with nerve injury induced pain (neuropathic pain) can be assessed in rats. Rats are tested prior to surgery to determine a baseline, or normal, PWT. Rats are tested again 2 to 3 weeks post-surgery, prior to, and at different times after (e.g. 1, 3, 5 and 24 hr) drug administration. An increase in PWT following drug administration indicates that the test compound reduces mechanical hyperalgesia.

Thermal Hyperalgesia:

The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," *Pain* 32(1): 77-88 (1988). The maximum exposure time is set at 32 seconds to avoid tissue damage and any directed paw withdrawal from the heat source is taken as the end point. Three latencies are determined at each time point and averaged. Only the affected (ipsilateral) paw is tested.

In Vivo Assay for Anticonvulsant Activity

The compounds of the present invention can be tested for in vivo anticonvulsant activity after i.v., p.o., or i.p. injection using any of a number of anticonvulsant tests in mice, including the maximum electroshock seizure test (MES). Maximum electroshock seizures are induced in male NSA mice weighing between 15-20 g and in male Sprague-Dawley rats weighing between 200-225 g by application of current (for mice: 50 mA, 60 pulses/sec, 0.8 msec pulse width, 1 sec duration, D.C.; for rats: 99 mA, 125 pulses/sec, 0.8 msec pulse width, 2 sec duration, D.C.) using a Ugo Basile ECT device (Model 7801). Mice are restrained by gripping the loose skin on their dorsal surface and saline-coated corneal electrodes are held lightly against the two corneae. Rats are allowed free movement on the bench top and ear-clip electrodes are used. Current is applied and animals are observed for a period of up to 30 seconds for the occurrence of a tonic hindlimb extensor response. A tonic seizure is defined as a hindlimb extension in excess of 90 degrees from the plane of the body. Results can be treated in a quantal manner.

Pharmaceutical Compositions

Although a peptide of the invention may be administered to a subject in the form of a raw chemical without any other components present, the peptide is preferably administered as part of a pharmaceutical composition containing the peptide combined with a suitable pharmaceutically acceptable carrier. Such a carrier can be selected from pharmaceutically acceptable excipients and auxiliaries appropriate for peptide compositions.

Pharmaceutical compositions within the scope of the present invention include all compositions where a peptide of the invention is combined with a pharmaceutically acceptable carrier. In a preferred embodiment, the peptide is present in the composition in an amount that is effective to achieve its intended therapeutic purpose. While individual subject needs may vary, a determination of optimal ranges of effective amounts of each peptide is within the skill of the art. Typically, the peptides may be administered to a subject, e.g., a human, at a dosage of about 0.01, 0.05, 0.1, 0.5, 1, 5, 10, 50, 100, or 500 μg/kg body weight, depending on the specific peptide selected, the desired therapeutic response, the route of administration, the formulation, the medical condition of the subject, and other factors known to those of skill in the art.

A pharmaceutical composition of the present invention can be administered to any subject that may experience the beneficial effects of a peptide of the invention. Foremost among such subjects are mammals, especially humans and companion animals, although the invention is not intended to be so limited.

A pharmaceutical composition of the present invention is preferably manufactured in a manner which itself will be known in view of the instant disclosure, for example, by means of conventional mixing, dissolving, formulating or lyophilizing processes.

A pharmaceutical composition of the present invention can contain from about 0.01 to 99 percent by weight, and preferably from about 0.25 to 75 percent by weight, of active peptide(s).

A method of the present invention, such as a method for treating a disorder or providing preemptive or palliative treatment of a disorder responsive to the blockade of sodium channels in a subject in need thereof, can further comprise administering a second therapeutic agent to the subject in combination with a peptide of the present invention. The other therapeutic agent is preferably administered in an effective amount.

Effective amounts of the other therapeutic agents will generally be known to or readily ascertainable by those skilled in the art. It is well within the skilled artisan's purview to determine the other therapeutic agent's optimal effective-amount range.

A peptide of the invention (i.e., the first therapeutic agent) and the second therapeutic agent can act additively or synergistically. Alternatively, the second therapeutic agent can be used to treat a disorder or condition that is different from the disorder or condition for which the first therapeutic agent is being administered. In one embodiment, a peptide of the invention is administered concurrently with a second therapeutic agent; for example, a single composition comprising both an effective amount of a peptide of the invention, and an effective amount of the second therapeutic agent can be administered. Accordingly, the present invention further provides a pharmaceutical composition comprising a combination of a peptide of the invention, the second therapeutic agent, and a pharmaceutically acceptable carrier. Alternatively, a first pharmaceutical composition comprising an effective amount of a peptide of the invention and a second pharmaceutical composition comprising an effective amount of the second therapeutic agent can be concurrently administered in two different compositions. In another embodiment, an effective amount of a peptide of the invention is administered prior or subsequent to administration of an effective amount of the second therapeutic agent. In this embodiment, the peptide of the invention is administered while the second therapeutic agent exerts its therapeutic effect, or the second therapeutic agent is administered while the peptide of the invention exerts its therapeutic effect for treating a disorder or condition or providing preemptive or palliative treatment of a disorder or condition.

The second therapeutic agent can be an opioid agonist, a non-opioid analgesic, a non-steroidal anti-inflammatory agent, an antimigraine agent, a Cox-II inhibitor, a β-adrenergic blocker, an anticonvulsant, an antidepressant, an anticancer agent, an agent for treating addictive disorder, an agent for treating Parkinson's disease and parkinsonism, an agent for treating anxiety, an agent for treating epilepsy, an agent for treating a seizure, an agent for treating a stroke, an agent for treating a pruritic condition, an agent for treating psychosis, an agent for treating ALS, an agent for treating a cognitive disorder, an agent for treating a migraine, an agent for treating vomiting, an agent for treating dyskinesia, or an agent for treating depression, or a mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papavereturn, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable salts thereof, and mixtures thereof.

Examples of useful non-opioid analgesics include nonsteroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, and pharmaceutically acceptable salts thereof, and mixtures thereof. Examples of other suitable non-opioid analgesics include the following, non limiting, chemical classes of analgesic, antipyretic, nonsteroidal antiinflammatory drugs: salicylic acid derivatives, including aspirin, sodium salicylate, choline magnesium trisalicylate, salsalate, diflunisal, salicylsalicylic acid, sulfasalazine, and olsalazin; para aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone. For a more detailed description of the NSAIDs, see Paul A. Insel, *Analgesic Antipyretic and Antiinflammatory Agents and Drugs Employed in the Treatment of Gout*, in Goodman & Gilman's *The Pharmacological Basis of Therapeutics* 617-57 (Perry B. Molinhoff and Raymond W. Ruddon eds., 9th ed 1996) and Glen R. Hanson, *Analgesic, Antipyretic and Anti Inflammatory Drugs* in Remington: *The Science and Practice of Pharmacy* Vol. II 1196-1221 (A. R. Gennaro ed. 19th ed. 1995) which are hereby incorporated by reference in their entireties. Suitable Cox-II inhibitors and 5-lipoxygenase inhibitors, as well as combinations thereof, are described in U.S. Pat. No. 6,136,839, which is hereby incorporated by reference in its entirety. Examples of useful Cox II inhibitors include, but are not limited to, rofecoxib and celecoxib.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, and mixtures thereof.

Examples of useful β-adrenergic blockers include, but are not limited to, acebutolol, alprenolol, amosulabol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol, indenolol, labetalol, levobunolol, mepindolol, metipranolol, metoprolol, moprolol, nadolol, nadoxolol, nebivalol, nifenalol, nipradilol, oxprenolol, penbutolol, pindolol, practolol, pronethalol, propranolol, sotalol, sulfinalol, talinolol, tertatolol, tilisolol, timolol, toliprolol, and xibenolol.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenyloin, mephobarbital, metharbital, methetoin, methsuximide, 5-methyl-5-(3-phenanthryl)-hydantoin, 3-methyl-5-phenylhydantoin, narcobarbital, nimetazepam, nitrazepam, oxcarbazepine, paramethadione, phenacemide, phenetharbital, pheneturide, phenobarbital, phensuximide, phenylmethylbarbituric acid, phenyloin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, and zonisamide.

Examples of useful antidepressants include, but are not limited to, binedaline, caroxazone, citalopram, (S)-citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

Examples of useful anticancer agents include, but are not limited to, acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, asperlin, azacitidine, azetepa, azotomycin, batimastat, benzodepa, bicalutamide, bisantrene hydrochloride, bisnafide dimesylate, bizelesin, bleomycin sulfate, brequinar sodium, bropirimine, busulfan, cactinomycin, calusterone, caracemide, carbetimer, carboplatin, carmustine, carubicin hydrochloride, carzelesin, cedefingol, chlorambucil, cirolemycin, and cisplatin.

Therapeutic agents useful for treating an addictive disorder include, but are not limited to, methadone, desipramine, amantadine, fluoxetine, buprenorphine, an opiate agonist, 3-phenoxypyridine, or a serotonin antagonist.

Examples of useful therapeutic agents for treating Parkinson's disease and parkinsonism include, but are not limited to, carbidopa/levodopa, pergolide, bromocriptine, ropinirole, pramipexole, entacapone, tolcapone, selegiline, amantadine, and trihexyphenidyl hydrochloride.

Examples of useful therapeutic agents for treating anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; and propanediol carbamates, such as meprobamate and tybamate.

Examples of useful therapeutic agents for treating epilepsy or seizure include, but are not limited to, carbamazepine, ethosuximide, gabapentin, lamotrigine, phenobarbital, phenyloin, primidone, valproic acid, trimethadione, benzodiazepines, gamma-vinyl GABA, acetazolamide, and felbamate.

Examples of useful therapeutic agents for treating a pruritic condition include, but are not limited to, naltrexone; nalmefene; danazol; tricyclics such as amitriptyline, imipramine, and doxepin; antidepressants such as those given below; menthol; camphor; phenol; pramoxine; capsaicin; tar; steroids; and antihistamines.

Examples of useful therapeutic agents for treating psychosis include, but are not limited to, phenothiazines such as chlorpromazine hydrochloride, mesoridazine besylate, and thoridazine hydrochloride; thioxanthenes such as chloroprothixene and thiothixene hydrochloride; clozapine; risperidone; olanzapine; quetiapine; quetiapine fumarate; haloperidol; haloperidol decanoate; loxapine succinate; molindone hydrochloride; pimozide; and ziprasidone.

Examples of useful therapeutic agents for treating cognitive disorders include, but are not limited to, agents for treating dementia such as tacrine; donepezil; ibuprofen; antipsychotic drugs such as thioridazine and haloperidol; and antidepressant drugs such as those given below.

Examples of useful therapeutic agents for treating a migraine include, but are not limited to, sumatriptan; methysergide; ergotamine; caffeine; and beta-blockers such as propranolol, verapamil, and divalproex.

Examples of useful therapeutic agents for treating vomiting include, but are not limited to, 5-HT3 receptor antagonists such as ondansetron, dolasetron, granisetron, and tropisetron; dopamine receptor antagonists such as prochlorperazine, thiethylperazine, chlorpromazine, metoclopramide, and domperidone; glucocorticoids such as dexamethasone; and benzodiazepines such as lorazepam and alprazolam.

Examples of useful therapeutic agents for treating dyskinesia include, but are not limited to, reserpine and tetrabenazine.

Examples of useful therapeutic agents for treating depression include, but are not limited to, tricyclic antidepressants such as amitryptyline, amoxapine, bupropion, clomipramine, desipramine, doxepin, imipramine, maprotiline, nefazadone, nortriptyline, protriptyline, trazodone, trimipramine, and venlafaxine; selective serotonin reuptake inhibitors such as citalopram, (S)-citalopram, fluoxetine, fluvoxamine, paroxetine, and setraline; monoamine oxidase inhibitors such as isocarboxazid, pargyline, phenelzine, and tranylcypromine; and psychostimulants such as dextroamphetamine and methylphenidate.

SEQUENCES

The present invention provides the following specific peptides comprising the amino acid sequences of SEQ ID NOS: 1-15, and the pharmaceutically acceptable salts, prodrugs and solvates thereof. If an amino acid residue is not set forth at position 30 and/or position 31, relative to SEQ ID NO: 1, then $Xaa_{30}$ and/or $Xaa_{31}$ are absent.

SEQ ID NO: 1 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Xaa_{12}$-$Arg_{13}$-$Lys_{14}$-$Cys_{15}$-$Cys_{16}$-$Glu_{17}$-$Gly_{18}$-$Xaa_{19}$-$Val_{20}$-$Cys_{21}$-$Arg_{22}$-$Leu_{23}$-$Trp_{24}$-$Cys_{25}$-$Lys_{26}$-$Lys_{27}$-$Xaa_{28}$-$Xaa_{29}$-$Xaa_{30}$-$Xaa_{31}$.

SEQ ID NO: 2 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$-$NH_2$.

SEQ ID NO: 3 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$.

-continued

SEQ ID NO: 4 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$.

SEQ ID NO: 5 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Ile_{28}$-$Ile_{29}$.

SEQ ID NO: 6 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$.

SEQ ID NO: 7 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$\alpha$-Me-$Leu_{29}$-$Trp_{30}$, wherein "Me" is "methyl."

SEQ ID NO: 8 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-N-Me-$Leu_{29}$-$Trp_{30}$.

SEQ ID NO: 9 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Ile_{29}$-$Leu_{30}$-$Trp_{31}$.

SEQ ID NO: 10 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Ile_{30}$.

SEQ ID NO: 11 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$\alpha$-Me-$Leu_{29}$-$Ile_{30}$.

SEQ ID NO: 12 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-N-Me-$Leu_{29}$-$Ile_{30}$.

SEQ ID NO: 13 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Ile_{28}$-$Leu_{29}$-$Trp_{30}$.

SEQ ID NO: 14 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Ile_{28}$-$Ile_{29}$-$Trp_{30}$.

SEQ ID NO: 15 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Leu_{28}$-$Trp_{29}$.

Other sequences discussed herein include the following peptide sequences. If an amino acid residue is not set forth at position 30 and/or position 31, relative to SEQ ID NO: 1, then $Xaa_{30}$ and/or $Xaa_{31}$ are absent.

SEQ ID NO: 16 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$ (ProTx II).

SEQ ID NO: 17 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Ile_{28}$-$Ile_{29}$ (PaTx I).

SEQ ID NO: 18 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Tyr_{19}$-$Val_{20}$-$Cys_{21}$-$Glu_{22}$-$Leu_{23}$-$Trp_{24}$-$Cys_{25}$-$Lys_{26}$-$Tyr_{27}$-$Asn_{28}$-$Leu_{29}$ (JzTx XII).

SEQ ID NO: 19 is $Tyr_1$-$Cys_2$-$Gln_3$-$Lys_4$-$Trp_5$-$Leu_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Asp_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Arg_{28}$-$Leu_{29}$ (GsAF I).

SEQ ID NO: 20 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Lys_{12}$-$Arg_{13}$-$Ala_{14}$-$Cys_{15}$-$Cys_{16}$-$Glu_{17}$-$Gly_{18}$-$Leu_{19}$-$Arg_{20}$-$Cys_{21}$-$Lys_{22}$-$Leu_{23}$-$Trp_{24}$-$Cys_{25}$-$Arg_{26}$-$Lys_{27}$-$Ile_{28}$-$Ile_{29}$ (JzTx V).

SEQ ID NO: 21 is $Tyr_1$-$Cys_2$-$Gln_3$-$Lys_4$-$Trp_5$-$Met_6$-$Trp_7$-$Thr_8$-$Cys_9$-$Asp_{10}$-$Glu_{11}$-$Glu_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Ile_{29}$-$Glu_{30}$-$Glu_{31}$-$Gly_{32}$ (VsTx II).

SEQ ID NO: 22 is $Tyr_1$-$Cys_2$-$Gln_3$-$Lys_4$-$Trp_5$-$Met_6$-$Trp_7$-$Thr_8$-$Cys_9$-$Asp_{10}$-$Glu_{11}$-$Glu_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Ile_{29}$-$Glu_{30}$-$Trp_{31}$ (GsAF II).

SEQ ID NO: 23 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Lys_{12}$-$Arg_{13}$-$Lys_{14}$-$Cys_{15}$-$Cys_{16}$-$Glu_{17}$-$Asp_{18}$-$Met_{19}$-$Val_{20}$-$Cys_{21}$-$Gln_{22}$-$Leu_{23}$-$Trp_{24}$-$Cys_{25}$-$Lys_{26}$-$Lys_{27}$-$Arg_{28}$-$Leu_{29}$ (GrTx I).

SEQ ID NO: 24 is $Tyr_1$-$Cys_2$-$Gln_3$-$Lys_4$-$Trp_5$-$Met_6$-$Trp_7$-$Thr_8$-$Cys_9$-$Asp_{10}$-$Glu_{11}$-$Glu_{12}$-$Arg_{13}$-$Lys_{14}$-$Cys_{15}$-$Cys_{16}$-$Glu_{17}$-$Gly_{18}$-$Leu_{19}$-$Val_{20}$-$Cys_{21}$-$Arg_{22}$-$Leu_{23}$-$Trp_{24}$-$Cys_{25}$-$Lys_{26}$-$Arg_{27}$-$Ile_{28}$-$Ile_{29}$-$Asn_{30}$-$Met_{31}$ (GsMtx II/PaTX II).

SEQ ID NO: 25 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Ala_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$.

SEQ ID NO: 26 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Ala_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Trp_{30}$.

SEQ ID NO: 27 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Ala_{28}$-$Leu_{29}$-$Trp_{30}$-$Xaa_{31}$.

SEQ ID NO: 28 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Ala_{29}$-$Trp_{30}$.

-continued

SEQ ID NO: 29 is $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Glu_{12}$-$Arg_{13}$-$Lys_{14}$-$Cys_{15}$-$Cys_{16}$-$Glu_{17}$-$Gly_{18}$-$Met_{19}$-$Val_{20}$-$Cys_{21}$-$Arg_{22}$-$Leu_{23}$-$Trp_{24}$-$Cys_{25}$-$Lys_{26}$-$Lys_{27}$-$Lys_{28}$-$Leu_{29}$-$Ala_{30}$.

The following examples are illustrative, but not limiting, of the peptides, compositions and methods of the present invention. Suitable modifications and adaptations of the variety of conditions and parameters normally encountered in clinical therapy and which are obvious to those skilled in the art in view of this disclosure are within the spirit and scope of the invention.

EXAMPLE 1

Synthesis of Peptides

Several peptides of SEQ ID NO: 1 set forth in Tables 2 and 3 were synthesized. Fmoc-L-amino acids and HCTU were purchased from Protein Technologies Inc. Resins were purchased from EMD chemicals (Fmoc-amino acid-NovaSyn resin) and Anaspec (H-amino acid-2-Cl-Trt resin and H-Trp (Boc)-2-Cl-Trt resin). HPLC-graded solvents and Reagent-Plus®-graded reagents were purchased from Sigma-Aldrich. HATU was purchased from Genscript.

Linear peptides were obtained by the solid-phase technique ("Fmoc Solid Phase Peptide Synthesis, A Practical Approach," W. C. Chan and P. D. White, Oxford University Press (2000)) using an ABI 433 and a Pioneer peptide synthesizer.

Synthesis Route 1:

Peptides were assembled stepwise on 0.05-0.1 mmol of Fmoc-amino acid-NovaSyn resin (0.2-0.3 mmol/g) or Anaspec (H-amino acid-2-Cl-Trt resin (0.4-0.5 mmol/g)) using 5-10 fold excess of Fmoc amino acids. Fmoc protecting groups were removed using 20% piperidine in DMF and the free amine was coupled with amino acids/HCTU/NMM (1:1:2). The side-chain protecting groups used for trifunctional residues were: trityl for Cys, His, Asn and Gln; t-butyl for Asp, Glu, Ser, Thr and Tyr; 2,2,4,6,7-pentamethyldihydrobenzofuran-5-sulfonyl for Arg; and t-butyloxycarbonyl for Lys and Trp.

Linear peptide was treated with TFA:TIS:EDT or TFA:TIS:EDT:thioanisole:phenol:$H_2O$ (81.5:1:2.5:5:5:5 by volume) for 2 hours at room temperature to cleave from the resin. Cleaved peptides were treated with cold diethyl ether to precipitate peptides, and precipitated peptides were washed with diethyl ether three times. Crude linear peptides were purified by reversed Prep-HPLC and white solids were obtained.

Purified linear peptides (1 mg/10-20 mL) were dissolved in 0.1 M Tris/HCl buffer, 2.0 M Urea, 0.15 mM GSH, 0.3 mM GSSG, pH 8 (adjusted with Saturated Aqueous $NaHCO_3$) overnight and purified by reversed Prep-HPLC(C 18, 5 μm, 250 mm×21 mm, buffer; A: 0.1% v/v TFA in $H_2O$ and B: 0.1% v/v TFA in MeCN). Purified peptides were characterized by analytical LCMS and NMR.

Synthesis Route 2:

Peptides were assembled stepwise on 0.025-0.05 mmol of H-Trp(Boc)-2-Cl-Trt resin (0.42 mmol/g) using 8-16 fold excess of Fmoc amino acids. Fmoc protecting groups were removed using 20% piperidine in DMF and the free amine was coupled with amino acids/HATU/2,4,6-collidine. The side-chain protecting groups used for trifunctional residues were: trityl for Cys, His, Asn and Gln; t-butyl for Asp, Glu, Ser, Thr and Tyr; 2,2,4,6,7-pentamethyldihydrobenzofuran-5-sulfonyl for Arg; and t-butyloxycarbonyl for Lys and Trp.

Linear peptide was treated with TFA:TIS:3,6-Dioxa-1,8-octane-dithiol:thioanisole:phenol:$H_2O$ (81.5:1:2.5:5:5:5 by vol.) for 2 hours at room temperature to cleave from the resin. Cleaved peptides were treated with cold diethyl ether to precipitate peptides out and precipitated peptides were washed with diethyl ether for 3 times. Crude linear peptides were purified by reversed Prep-HPLC and white solids were obtained.

Purified linear peptides (1 mg/10 mL) were dissolved in 0.1 M of Tris/HCl buffer, 2.0 M of Urea, 0.15 mM of GSH, 0.3 mM of GSSG, pH 8 (adjusted with saturated aqueous $NaHCO_3$) overnight and purified by reversed Prep-HPLC (C18, 5 μm, 250 mm×21 mm, buffer; A: 0.1% v/v TFA in $H_2O$ and B: 0.1% v/v TFA in MeCN). Purified toxins were characterized by analytical LCMS and NMR.

TABLE 2

Peptides Of SEQ ID NO: 1

| Sequence | SEQ ID NO: | IC50 $Na_v1.7$ (nm) | IC50 $Na_v1.2$ (nm) |
|---|---|---|---|
| YCQKWMWTCDSERKCCEGMVCRLWCKKKLW-$NH_2$ | 2 | 1 | 8 ± 1 |
| YCQKWMWTCDSARKCCEGMVCRLWCKKKLW | 3 | 0.2 ± 0.03 | 8 ± 2 |
| YCQKWMWTCDSERKCCEGLVCRLWCKKKLW | 4 | 1.7 ± 0.1 | 44.7 ± 15 |
| YCQKWMWTCDSERKCCEGMVCRLWCKKII | 5 | 552 ± 90 | 919 ± 130 |
| YCQKWMWTCDSARKCCEGLVCRLWCKKKLW | 6 | 1 ± 0 | 24 ± 10 |
| YCQKWMWTCDSARKCCEGLVCRLWCKKK[aml]W | 7 | 8 ± 1 | 28 ± 6 |
| YCQKWMWTCDSARKCCEGLVCRLWCKKK[nml]W | 8 | 18 ± 0 | 51 ± 10 |

TABLE 2-continued

Peptides Of SEQ ID NO: 1

| Sequence | SEQ ID NO: | IC50 $Na_v1.7$ (nm) | IC50 $Na_v1.2$ (nm) |
|---|---|---|---|
| YCQKWMWTCDSARKCCEGLVCRLWCKKKILW | 9 | 1 ± 0 | 33 ± 0 |
| YCQKWMWTCDSARKCCEGLVCRLWCKKKLI | 10 | 4 ± 0 | 98 ± 10 |
| YCQKWMWTCDSARKCCEGLVCRLWCKKK[aml]I | 11 | 10 ± 1 | 342 ± 73 |
| YCQKWMWTCDSARKCCEGLVCRLWCKKK[nml]I | 12 | 528 ± 100 | 138 ± 40 |
| YCQKWMWTCDSARKCCEGLVCRLWCKKILW | 13 | 3 ± 0 | 50 ± 10 |
| YCQKWMWTCDSARKCCEGLVCRLWCKKIIW | 14 | 5 ± 1 | 45 ± 0 |
| YCQKWMWTCDSARKCCEGLVCRLWCKKLW | 15 | 67 ± 0 | 63 ± 0 |

TABLE 3

Natural Toxins

| Sequence | Name | SEQ ID NO: | IC50 $Na_v1.7$ (nm) | IC50 $Na_v1.2$ (nm) |
|---|---|---|---|---|
| YCQKWMWTCDSERKCCEGMVCRLWCKKKLW | ProTx II | 16 | 1 | 105 ± 20 |
| YCQKWMWTCDSARKCCEGLVCRLWCKKII | PaTx I | 17 | 423 ± 110 | 5000 |
| YCQKWMWTCDSERKCCEGYVCELWCKYNL | JzTx XII | 18 | 1,527 ± 130 | 73,939 ± 14,440 |
| YCQKWLWTCDSERKCCEDMVCRLWCKKRL | GsAF I | 19 | 249 ± 20 | 255 ± 43 |
| YCQKWMWTCDSKRACCEGLRCKLWCRKII | JzTx V | 20 | 14 ± 10 | 157 ± 20 |
| YCQKWMWTCDEERKCCEGLVCRLWCKKKIEEG | VsTx II | 21 | 9,261 ± 2,210 | 42,409 ± 10,010 |
| YCQKWMWTCDEERKCCEGLVCRLWCKKKIEW | GsAF II | 22 | 70 ± 10 | 410 ± 20 |
| YCQKWMWTCDSKRKCCEDMVCQLWCKKRL | GrTx I | 23 | 1,007 ± 600 | 2,690 ± 460 |
| YCQKWMWTCDEERKCCEGLVCRLWCKRIINM | GsMTx II/ PaTX II | 24 | 260 ± 50 | 2,699 ± 790 |

EXAMPLE 2

Sodium Channel Assays

The peptides of SEQ ID NO: 1 set forth in Table 2 and the natural toxins set forth in Table 3 were assayed for sodium channel-blocking activity. As shown in Table 2, peptides of the present invention are potent antagonists of the Nav1.7 sodium channel. In addition, the peptides show selectivity as $Na_v1.7$ channel blockers, relative to $Na_v1.2$.

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. An isolated peptide comprising the amino acid sequence $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Xaa_{12}$-$Arg_{13}$-$Lys_{14}$-$Cys_{15}$-$CyS_{16}$-$Glu_{17}$-$Gly_{18}$-$Xaa_{19}$-$Val_{20}$-$Cys_{21}$-$Arg_{22}$-$Leu_{23}$-$Trp_{24}$-$Cys_{25}$-$Lys_{26}$-$Lys_{27}$-$Xaa_{28}$-$Xaa_{29}$-$Xaa_{30}$-$Xaa_{31}$ (SEQ ID NO: 1), or a pharmaceutically acceptable salt thereof, wherein each of $Xaa_{28}$ and $Xaa_{29}$ is any natural or modified amino acid residue;

$Xaa_{12}$ is an alanine residue;

$Xaa_{19}$ is a leucine residue;

$Xaa_{30}$ is any natural or modified amino acid residue or is absent; and $Xaa_{31}$ is any natural or modified amino acid residue or is absent, and wherein said isolated peptide is not PaTx I (SEQ ID NO: 17).

2. The isolated peptide of claim 1, wherein $Xaa_{31}$ is absent.

3. The isolated peptide of claim 1, wherein $Xaa_{30}$ and $Xaa_{31}$ are absent.

4. The isolated peptide of claim 1, wherein $Xaa_{28}$ is a lysine residue or an isoleucine residue.

5. The isolated peptide of claim 1, wherein $Xaa_{29}$ is a leucine residue, an isoleucine residue, an alpha-methylated leucine residue, an N-methylated leucine residue, or a tryptophan residue.

6. The isolated peptide of claim 1, wherein $Xaa_{30}$ is present and is tryptophan modified with an amino group, a tryptophan residue, a leucine residue, or an isoleucine residue.

7. The isolated peptide of claim 1, wherein $Xaa_{31}$ is present and is a tryptophan residue.

8. The isolated peptide of claim 1, wherein $Xaa_{12}$ is an alanine residue, each of $Xaa_{28}$ and $Xaa_{29}$ is any natural or modified amino acid residue;

$Xaa_{30}$ is any natural or modified amino acid residue or is absent; and $Xaa_{31}$ is absent.

9. The isolated peptide of claim 1, wherein $Xaa_{19}$ is a leucine residue;

each of $Xaa_{28}$ and $Xaa_{29}$ is any natural or modified amino acid residue;

$Xaa_{30}$ is any natural or modified amino acid residue or is absent; and $Xaa_{31}$ is absent.

10. The isolated peptide of claim 1, wherein $Xaa_{12}$ is an alanine residue, $Xaa_{19}$ is a leucine residue;

each of $Xaa_{28}$ and $Xaa_{29}$ is any natural or modified amino acid residue;

$Xaa_{30}$ is any natural or modified amino acid residue or is absent; and $Xaa_{31}$ is absent.

11. The isolated peptide of claim 1, wherein $Xaa_{12}$ is an alanine residue, $Xaa_{19}$ is a leucine residue, $Xaa_{28}$ is a lysine residue, $Xaa_{29}$ is a leucine residue, $Xaa_{30}$ is a tryptophan residue, and $Xaa_{31}$ is absent (SEQ ID NO: 6).

12. The isolated peptide of claim 1, wherein $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is a tryptophan residue, and $Xaa_{31}$ is absent (SEQ ID NO: 7).

13. The isolated peptide of claim 1, wherein $Xaa_{12}$ is an alanine residue, $Xaa_{19}$ is a leucine residue, $Xaa_{28}$ is a lysine residue, $Xaa_{29}$ is an N-methylated leucine residue, $Xaa_{30}$ is a tryptophan residue, and $Xaa_{31}$ is absent (SEQ ID NO: 8).

14. The isolated peptide of claim 1, wherein $Xaa_{12}$ is an alanine residue, $Xaa_{19}$ is a leucine residue, $Xaa_{28}$ is a lysine residue, $Xaa_{29}$ is an isoleucine residue, $Xaa_{30}$ is a leucine residue, and $Xaa_{31}$ is a tryptophan residue (SEQ ID NO: 9).

15. The isolated peptide of claim 1, wherein $Xaa_{12}$ is an alanine residue, $Xaa_{19}$ is a leucine residue, $Xaa_{28}$ is a lysine residue, $Xaa_{29}$ is a leucine residue, $Xaa_{30}$ is an isoleucine residue, and $Xaa_{31}$ is absent (SEQ ID NO: 10).

16. The isolated peptide of claim 1, wherein $Xaa_{12}$ is an alanine residue, $Xaa_{19}$ is a leucine residue, $Xaa_{28}$ is a lysine residue, $Xaa_{29}$ is an alpha-methylated leucine residue, $Xaa_{30}$ is an isoleucine residue, and $Xaa_{31}$ is absent (SEQ ID NO: 11).

17. The isolated peptide of claim 1, wherein $Xaa_{12}$ is an alanine residue, $Xaa_{19}$ is a leucine residue, $Xaa_{2s}$ is a lysine residue, $Xaa_{29}$ is an N-methylated leucine residue, $Xaa_{30}$ is an isoleucine residue, and $Xaa_{31}$ is absent (SEQ ID NO: 12).

18. The isolated peptide of claim 1, wherein $Xaa_{12}$ is an alanine residue, $Xaa_{19}$ is a leucine residue, $Xaa_{2s}$ is an isoleucine residue, $Xaa_{29}$ is a leucine residue, $Xaa_{30}$ is a tryptophan residue, and $Xaa_{31}$ is absent (SEQ ID NO: 13).

19. The isolated peptide of claim 1, wherein $Xaa_{12}$ is an alanine residue, $Xaa_{19}$ is a leucine residue, $Xaa_{2s}$ is an isoleucine residue, $Xaa_{29}$ is an isoleucine residue, $Xaa_{30}$ is a tryptophan residue, and $Xaa_{31}$ is absent (SEQ ID NO: 14).

20. The isolated peptide of claim 1, wherein $Xaa_{12}$ is an alanine residue, $Xaa_{19}$ is a leucine residue, $Xaa_{2s}$ is a lysine residue, $Xaa_{29}$ is a tryptophan residue, $Xaa_{30}$ is absent, and $Xaa_{31}$ is absent (SEQ ID NO: 15).

21. The isolated peptide of claim 1, wherein said isolated peptide is a recombinant peptide.

22. The isolated peptide of claim 1, wherein said isolated peptide is a chemically synthesized peptide.

23. The isolated peptide of claim 1, which is selected from the group consisting of SEQ ID NOs: 6, 7, 8, 9, 10, 11, 12, 13, 14, 15, and their pharmaceutically acceptable salts.

24. The isolated peptide of claim 1, which is selected from the group consisting of SEQ ID NOs: 6, 7, 8, 9, 10, 11, 13, 14, and their pharmaceutically acceptable salts.

25. The isolated peptide of claim 1, wherein said isolated peptide contains three cystine bridges with the connectivity $C_2$ to $C_{16}$, $C_9$ to $C_{21}$ and $C_{15}$ to $C_{25}$.

26. The isolated peptide of claim 1, wherein said isolated peptide inhibits Nav1.7 ion channel activity.

27. The isolated peptide of claim 1, wherein said isolated peptide selectively inhibits Nav1.7 ion channel activity relative to Nav1.2 ion channel activity.

28. The isolated peptide of claim 27, which is selected form the group consisting of SEQ ID NOs: 6, 7, 8, 9, 10, 11, 13, 14, and their pharmaceutically acceptable salts.

29. The isolated peptide of claim 1, wherein said amino acid sequence of SEQ ID NO: 1 is derivatized with an amino acid residue or a chemical moiety at the N-terminal amino acid residue and/or at the C-terminal amino acid residue.

30. A container comprising the isolated peptide of claim 1.

31. A pharmaceutical composition comprising the isolated peptide of claim 1 and a pharmaceutically acceptable carrier.

32. A container comprising the pharmaceutical composition of claim 31.

33. An article of manufacture comprising a plurality of containers, each of said containers comprising the pharmaceutical composition of claim 31.

34. A method of treating pain, said method comprising administering an effective amount of the isolated peptide of claim 1 to a subject in need thereof.

35. The method of claim 34, wherein said pain is neuropathic pain.

36. The method of claim 34, wherein said pain is chronic pain.

37. The method of claim 34, wherein said pain is acute pain.

38. The method of claim 34, wherein said pain is inflammatory pain.

39. The method of claim 34, wherein said pain is surgical pain.

40. The method of claim 34, wherein said isolated peptide is administered intrathecally to said subject.

41. A polynucleotide molecule comprising a nucleotide sequence encoding an amino acid sequence of $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Xaa_{12}$-$Arg_{13}$-$Lys_{14}$-$Cys_{15}$-$Cys_{16}$-$Glu_{17}$-$Gly_{18}$-$Xaa_{19}$-$Val_{20}$-$Cys_{21}$-$Arg_{22}$-$Leu_{23}$-$Trp_{24}$-$Cys_{25}$-$Lys_{26}$-$Lys_{27}$-$Xaa_{28}$-$Xaa_{29}$-$Xaa_{30}$-$Xaa_{31}$ (SEQ ID NO: 1), wherein each of $Xaa_{28}$ and $Xaa_{29}$, is any natural amino acid residue;

$Xaa_{12}$ is an alanine residue;

$Xaa_{19}$ is a leucine residue;

$Xaa_{30}$ is any natural amino acid residue or is absent; and $Xaa_{31}$ is any natural amino acid residue or is absent, wherein said amino acid sequence is not SEQ ID NO: 17.

42. A host cell comprising a vector, wherein said vector comprises a polynucleotide molecule, and wherein the polynucleotide molecule comprises a nucleotide sequence encoding an amino acid sequence of $Tyr_1$-$Cys_2$-$Gln_3$-$Lys_4$-$Trp_5$-$Met_6$-$Trp_7$-$Thr_8$-$Cys_9$-$Asp_{10}$-$Ser_{11}$-$Xaa_{12}$-$Arg_{13}$-$Lys_{14}$-$Cys_{15}$-$Cys_{16}$-$Glu_{17}$-$Gly_{18}$-$Xaa_{19}$-$Val_{20}$-$Cys_{21}$-$Arg_{22}$-$Leu_{23}$-$Trp_{24}$-$Cys_{25}$-$Lys_{26}$-$Lys_{27}$-$Xaa_{28}$-$Xaa_{29}$-$Xaa_{30}$-$Xaa_{31}$ (SEQ ID NO: 1), wherein each of $Xaa_{28}$ and $Xaa_{29}$ is any natural amino acid residue;

$Xaa_{12}$ is an alanine residue;

$Xaa_{19}$ is a leucine residue;

$Xaa_{30}$ is any natural amino acid residue or is absent; and $Xaa_{31}$ is any natural amino acid residue or is absent, wherein said amino acid sequence is not SEQ ID NO: 17.

* * * * *